(12) United States Patent
Honig

(10) Patent No.: US 11,116,609 B2
(45) Date of Patent: Sep. 14, 2021

(54) DENTAL IMPLANT DEVICE, SYSTEM AND METHOD OF USE

(71) Applicant: Iulian Honig, Bucharest (RO)

(72) Inventor: Iulian Honig, Bucharest (RO)

(73) Assignee: ABRACADABRA IMPLANTS LTD, Bat Yam (IL)

( * ) Notice: Subject to any disclaimer, the term of this patent is extended or adjusted under 35 U.S.C. 154(b) by 0 days.

(21) Appl. No.: 14/896,379

(22) PCT Filed: Jun. 6, 2014

(86) PCT No.: PCT/IL2014/050511
§ 371 (c)(1),
(2) Date: Dec. 5, 2015

(87) PCT Pub. No.: WO2014/195955
PCT Pub. Date: Dec. 11, 2014

(65) Prior Publication Data
US 2016/0113739 A1      Apr. 28, 2016

Related U.S. Application Data

(60) Provisional application No. 61/831,633, filed on Jun. 6, 2013.

(51) Int. Cl.
*A61C 9/00*      (2006.01)
*A61C 8/00*      (2006.01)
*A61B 90/00*     (2016.01)

(52) U.S. Cl.
CPC ............ *A61C 8/008* (2013.01); *A61C 8/0001* (2013.01); *A61C 8/006* (2013.01); *A61C 8/0074* (2013.01);
(Continued)

(58) Field of Classification Search
CPC ....... A61C 8/008; A61C 8/0001; A61C 8/006; A61C 8/0074; A61C 8/0089;
(Continued)

(56) References Cited

U.S. PATENT DOCUMENTS 984,782 A * 2/1911 Starr ...................... A61C 13/30
                                                            433/221
4,205,443 A * 6/1980 Weissman .............. A61C 9/002
                                                             433/74
(Continued)

FOREIGN PATENT DOCUMENTS

EP           0864299        *  9/1998

*Primary Examiner* — Edward Moran
*Assistant Examiner* — Matthew P Saunders
(74) *Attorney, Agent, or Firm* — The Law Office of Joseph L. Felber

(57) ABSTRACT

A dental device and a method of use for associating with an implanted dental implant anchor immediately following implantation. The device provides for projecting the implant's location, orientation and axis such that the device is readily visible to the naked eye by way of visual inspection so as to reveal the location of the implanted dental implant anchor following a healing period. The device having a distal portion, for coupling to the dental implant, a medial portion, for covering the proximal end of the dental implant, and a proximal portion, defining a vertically adjustable shaft provided for projecting the location, orientation and axis of implant anchor.

11 Claims, 14 Drawing Sheets

(52) U.S. Cl.
CPC ............ *A61C 8/0089* (2013.01); *A61C 9/004* (2013.01); *A61B 2090/3904* (2016.02); *A61B 2090/3937* (2016.02)

(58) Field of Classification Search
CPC ... A61C 8/0083; A61C 8/0093; A61C 8/0039; A61C 8/005; A61C 8/0054; A61C 8/0063; A61C 8/0066; A61C 9/004; A61C 9/00; A61C 9/006; A61C 9/002
USPC .................... 433/172–176, 201.1; 604/890.1
See application file for complete search history.

(56) References Cited

U.S. PATENT DOCUMENTS

| | | | | |
|---|---|---|---|---|
| 4,799,886 A * | 1/1989 | Wimmer | ............ | A61C 8/0019 433/176 |
| 4,976,739 A * | 12/1990 | Duthie, Jr. | ........... | A61C 8/0022 433/174 |
| 5,215,460 A * | 6/1993 | Perry | ................... | A61C 1/084 433/173 |
| 5,302,122 A * | 4/1994 | Milne | ................... | A61C 1/084 433/173 |
| 5,348,476 A * | 9/1994 | Cohen | ................ | A61C 13/0003 433/220 |
| 5,741,133 A * | 4/1998 | Gordils | ................ | A61C 1/084 433/76 |
| 5,951,287 A * | 9/1999 | Hawkinson | ............ | A61C 8/005 433/141 |
| 5,989,028 A * | 11/1999 | Niznick | ............... | A61C 8/0022 433/173 |
| 6,068,478 A * | 5/2000 | Grande | ............... | A61C 8/0001 433/172 |
| 6,068,479 A * | 5/2000 | Kwan | ................. | A61C 8/0001 433/173 |
| 6,386,876 B1 * | 5/2002 | Lee | ..................... | A61C 8/0001 433/173 |
| 6,464,500 B1 * | 10/2002 | Popovic | .............. | A61C 8/0022 433/173 |
| 6,592,370 B2 * | 7/2003 | Morgan | ................. | A61C 8/005 433/173 |
| 6,610,079 B1 * | 8/2003 | Li | .................... | A61B 17/00491 606/213 |
| 6,926,525 B1 * | 8/2005 | Rønvig | ................. | A61C 1/084 433/76 |
| 2001/0012606 A1 * | 8/2001 | Unger | ................... | A61C 8/001 433/173 |
| 2003/0082498 A1 * | 5/2003 | Halldin | ............... | A61C 8/0001 433/173 |
| 2003/0082499 A1 * | 5/2003 | Halldin | ............... | A61C 8/0001 433/173 |
| 2003/0170588 A1 * | 9/2003 | Augthun | .............. | A61C 8/0001 433/72 |
| 2003/0224328 A1 * | 12/2003 | Sapian | ................ | A61C 8/0077 433/173 |
| 2004/0029074 A1 * | 2/2004 | Brajnovic | ............. | A61C 1/084 433/172 |
| 2006/0014120 A1 * | 1/2006 | Sapian | ................ | A61C 8/0057 433/173 |
| 2006/0046229 A1 * | 3/2006 | Teich | ...................... | A61C 5/40 433/173 |
| 2009/0263760 A1 * | 10/2009 | Chung | ................... | A61C 8/005 433/173 |
| 2012/0156645 A1 * | 6/2012 | Jacoby | ................ | A61C 8/0062 433/173 |
| 2013/0196290 A1 * | 8/2013 | Herrington | ............ | A61C 8/006 433/173 |
| 2014/0193775 A1 * | 7/2014 | Hogan | ................. | A61C 8/0001 433/201.1 |
| 2014/0212845 A1 * | 7/2014 | Wadhwani | ............. | A61C 13/08 433/174 |

* cited by examiner

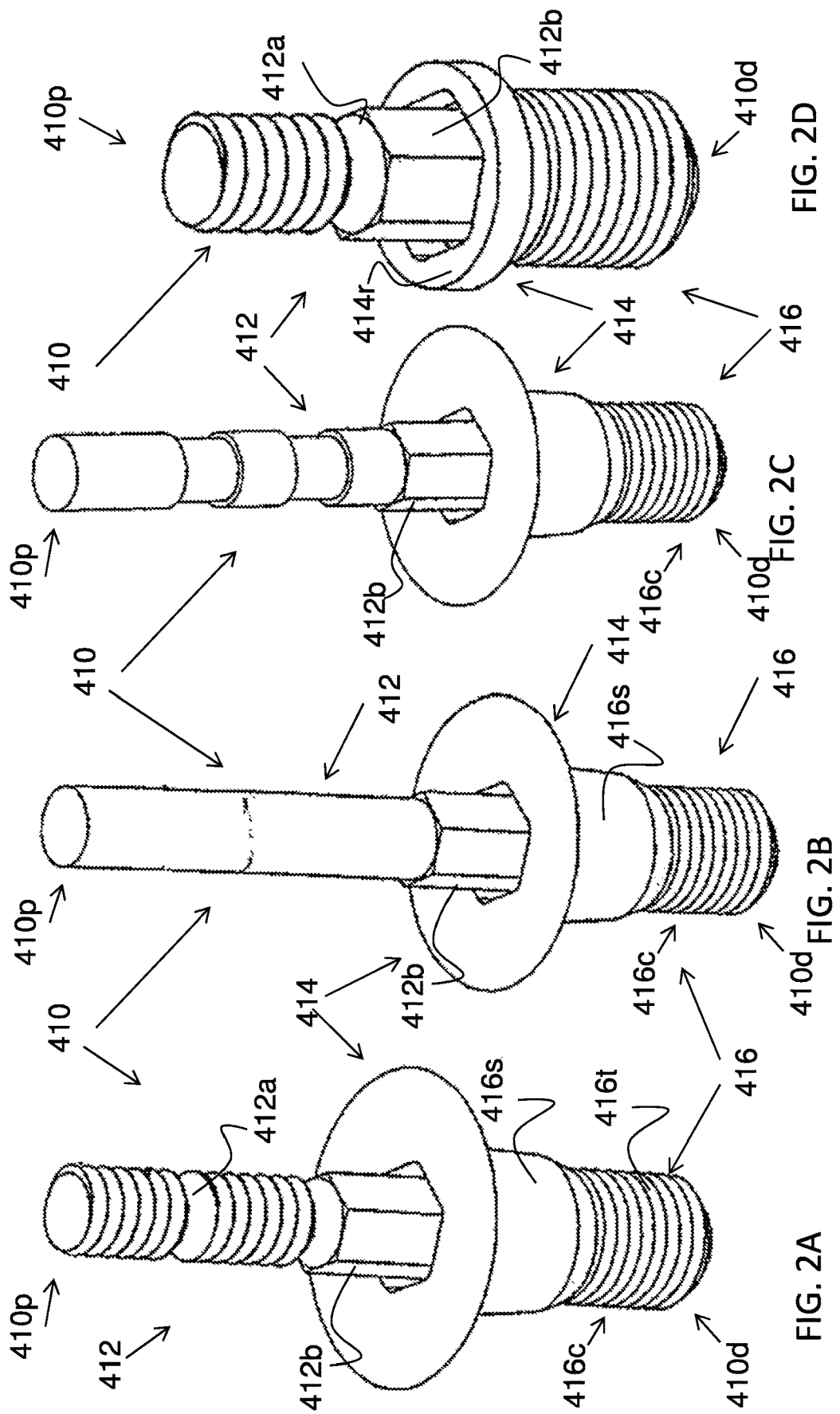

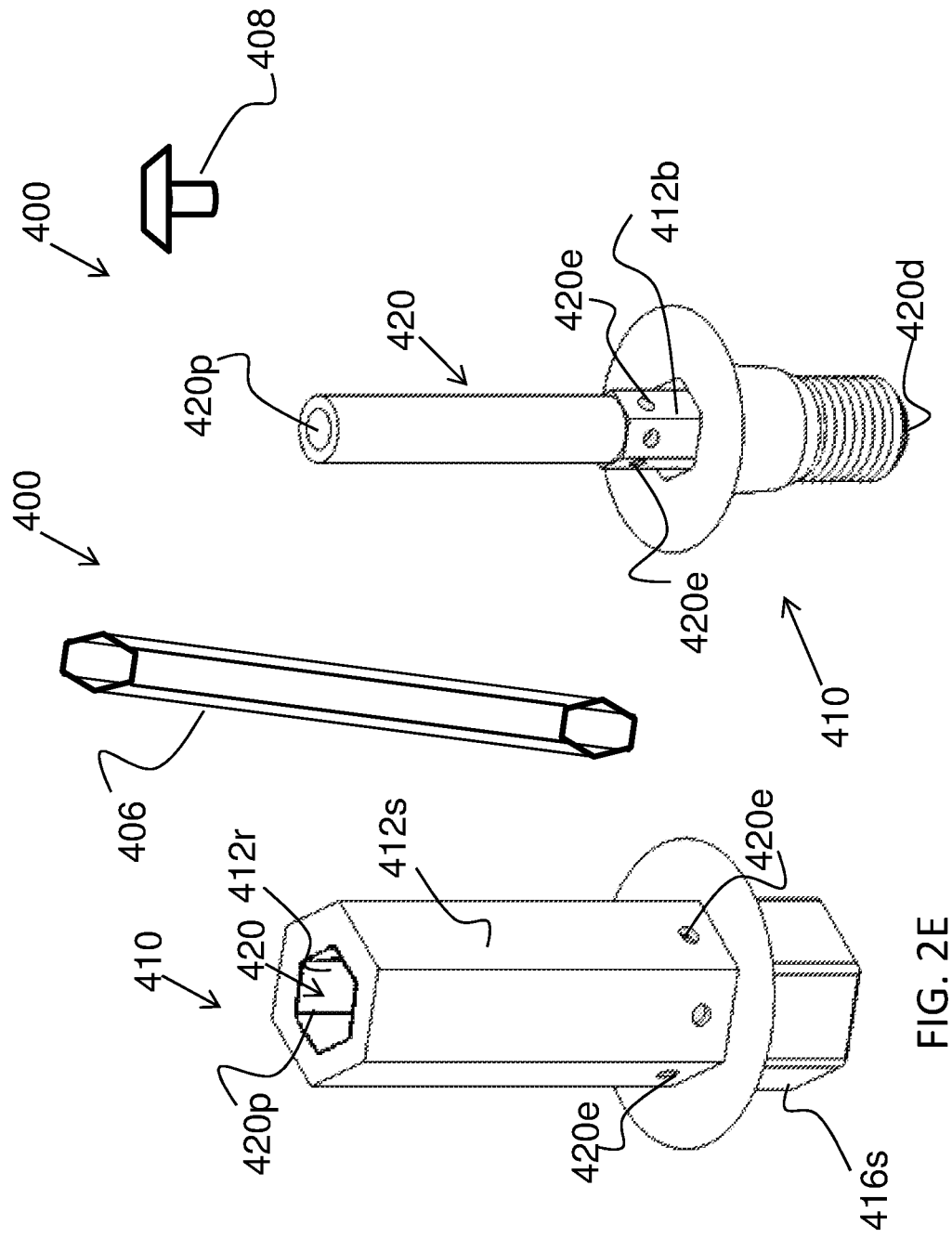

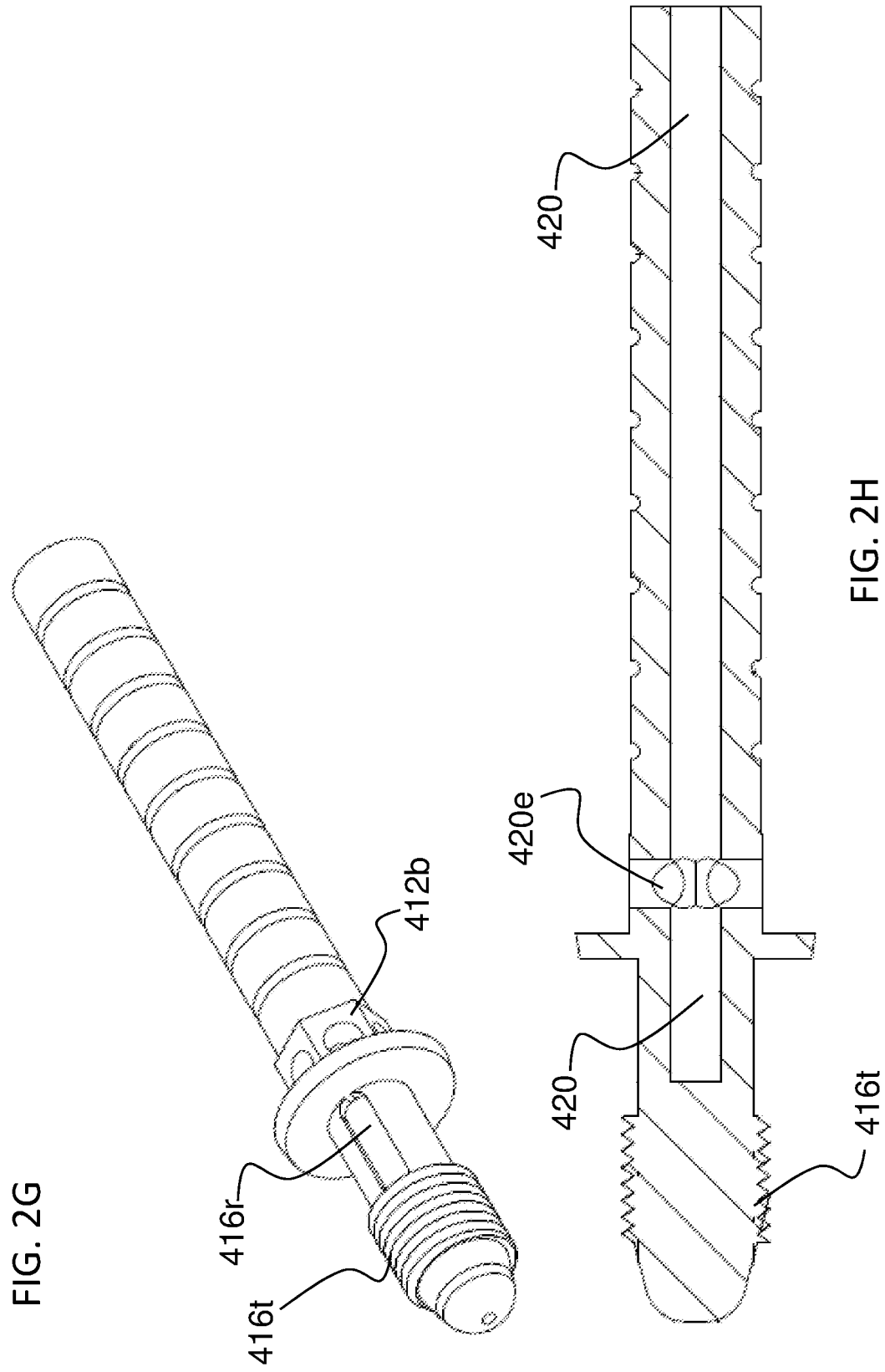

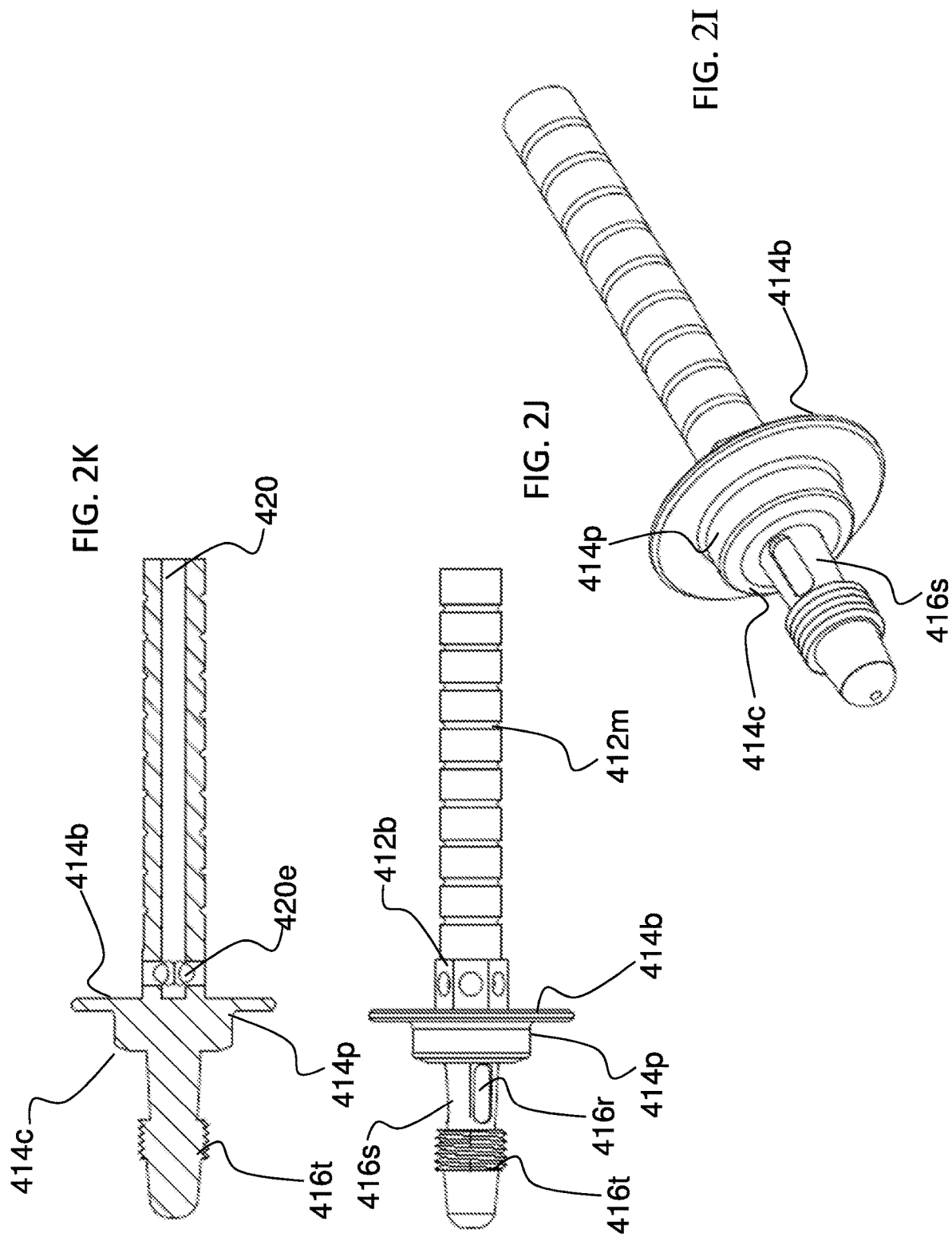

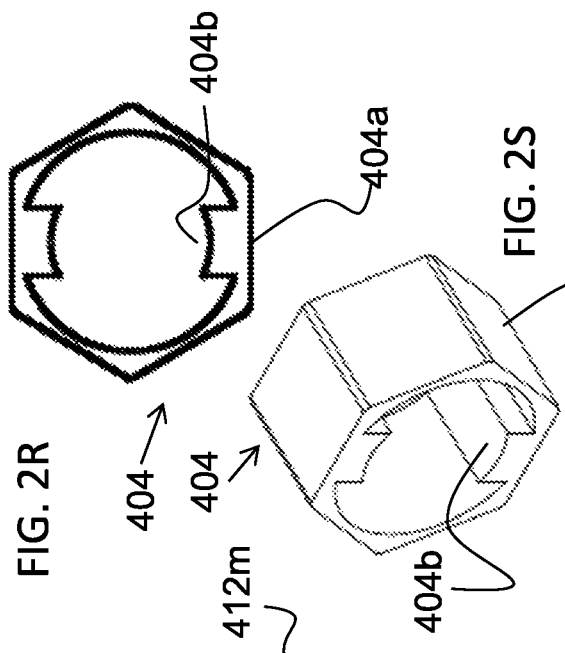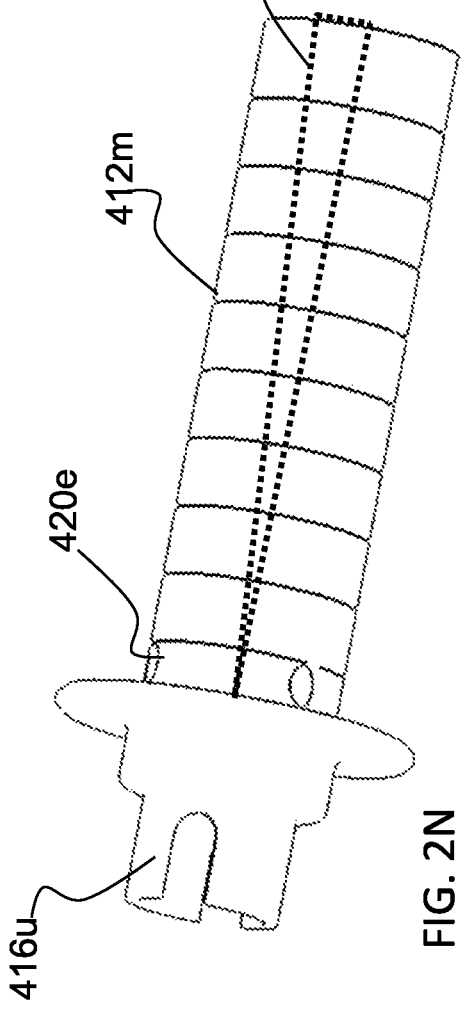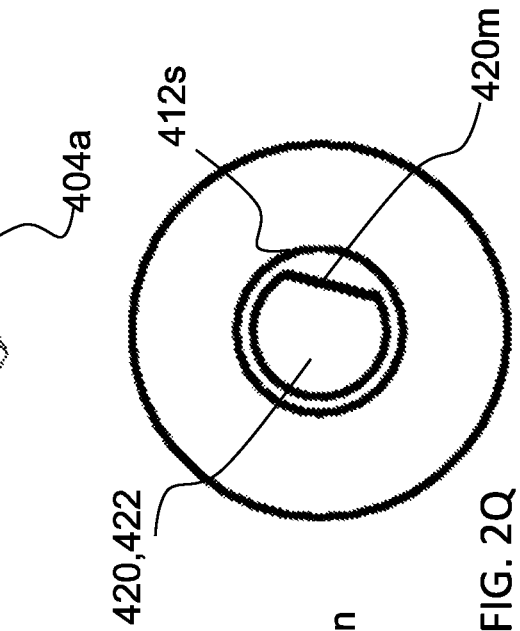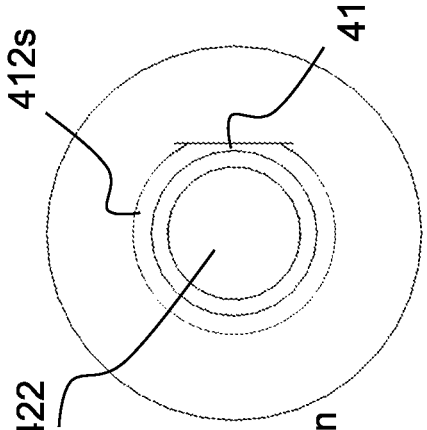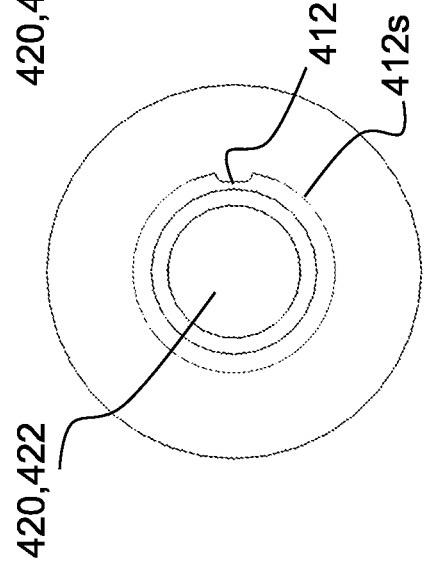

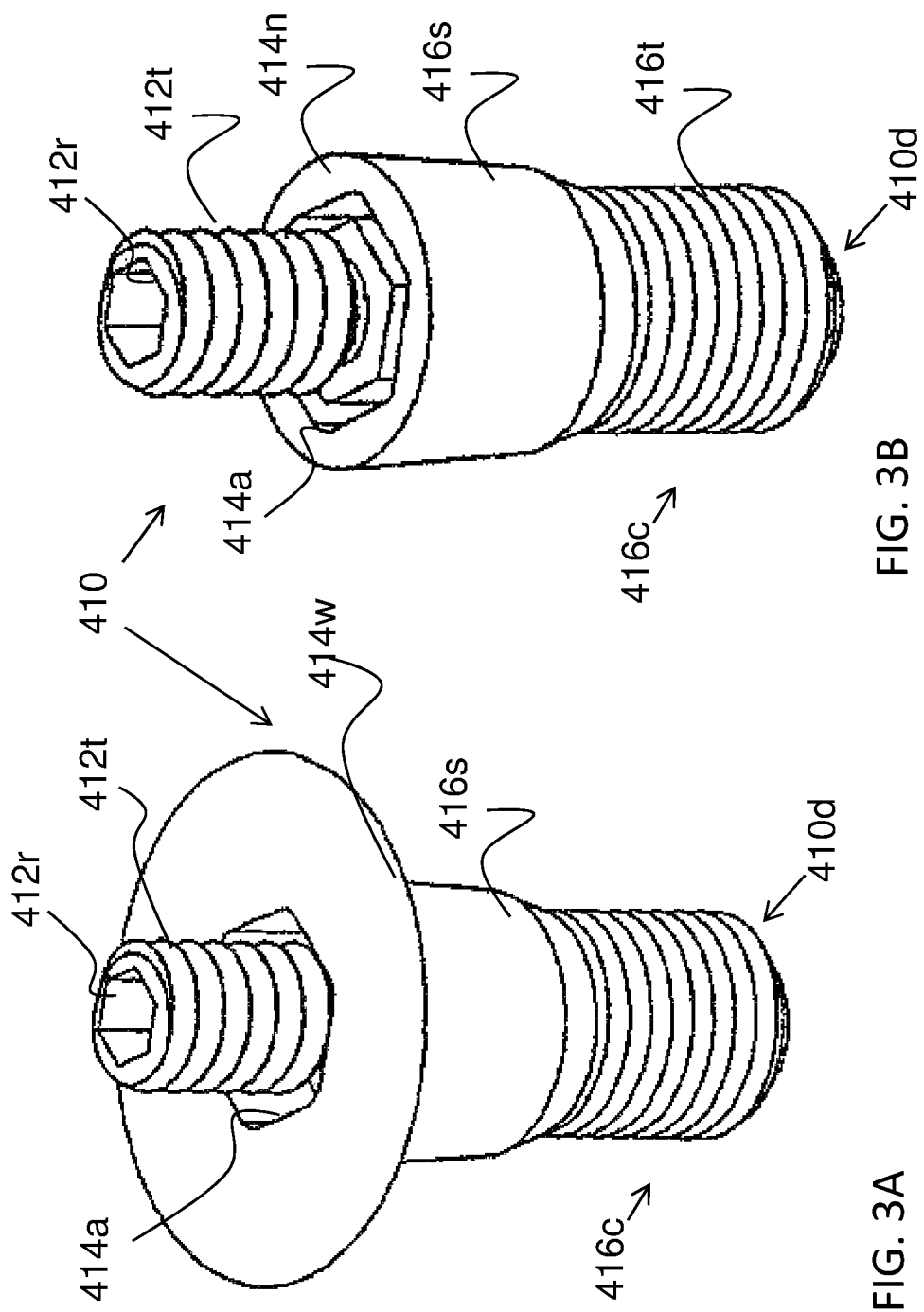

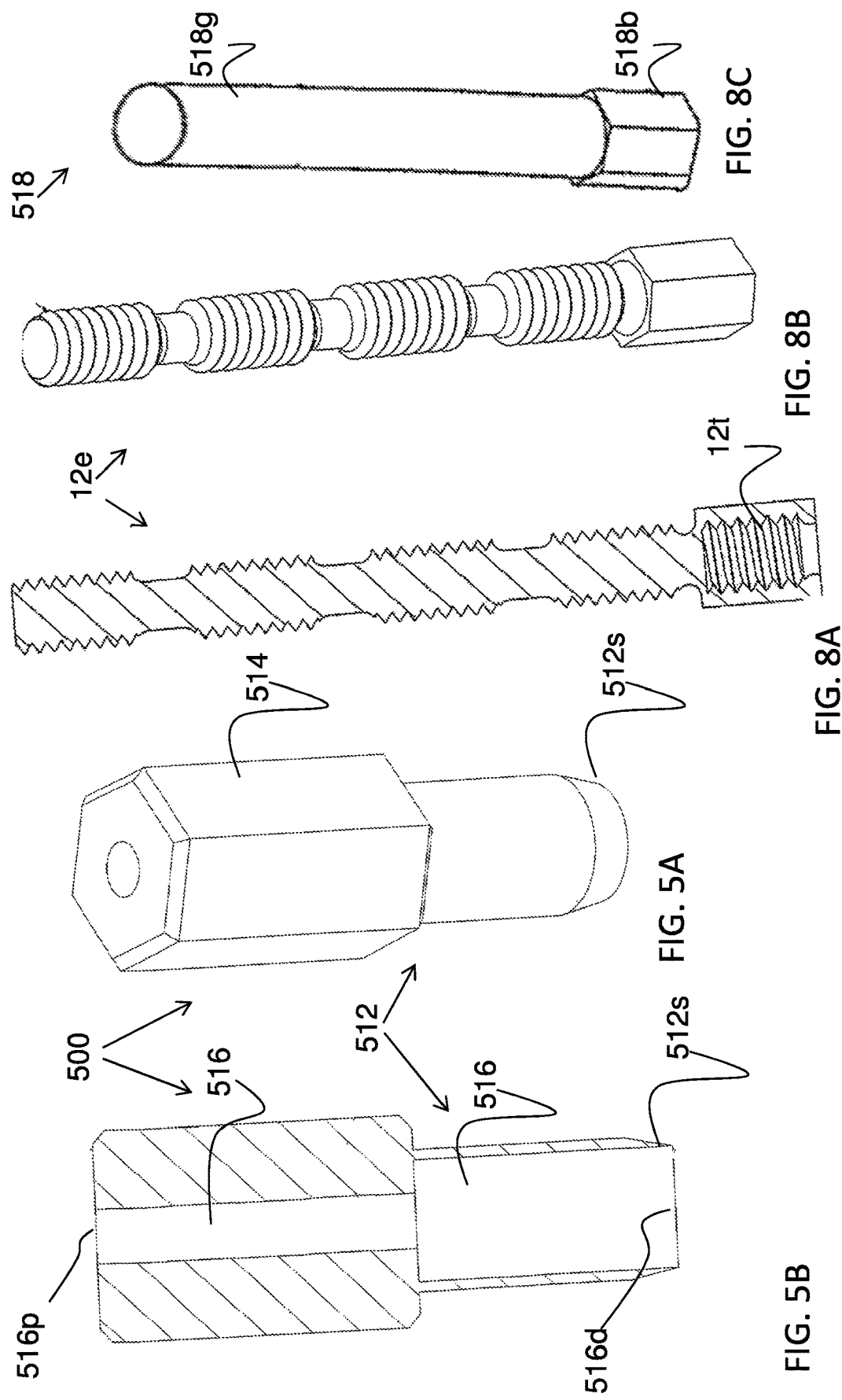

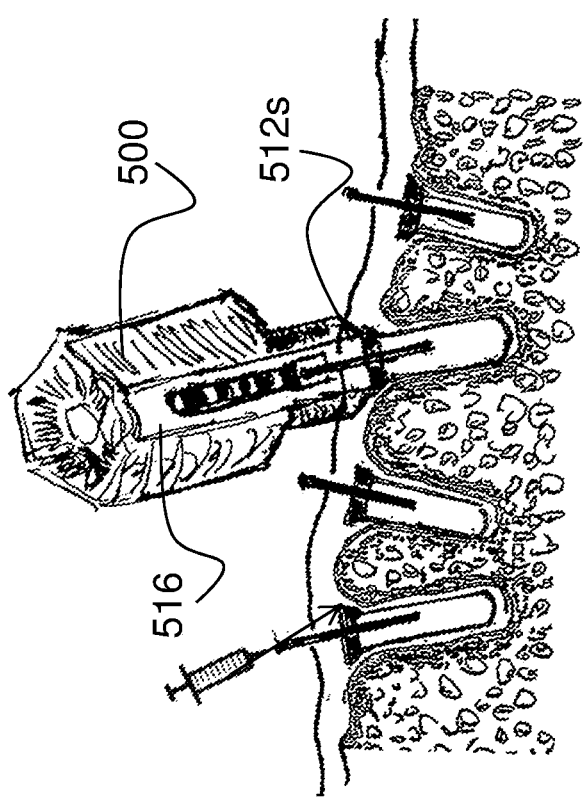
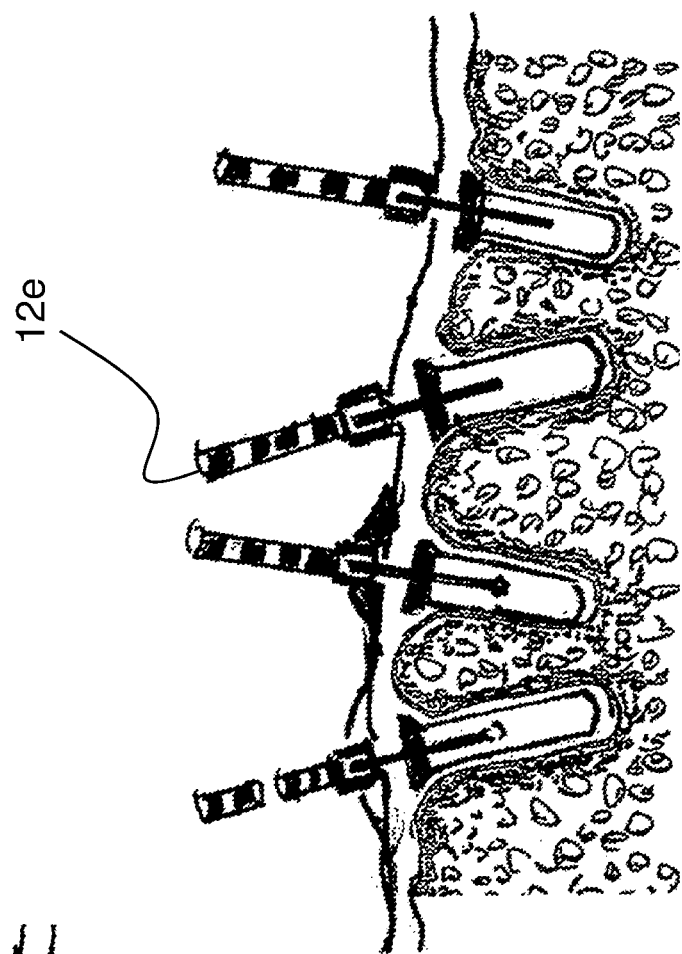
FIG. 6E
FIG. 6F

DENTAL IMPLANT DEVICE, SYSTEM AND METHOD OF USE

This Application is a national phase of, and claims priority from, PCT Application No. PCT/IL2014/050511, filed on Jun. 6, 2014, which claims priority from U.S. Provisional Application No. 61/831,633, filed Jun. 6, 2013, which is hereby incorporated by reference as if fully set forth herein.

FIELD OF THE INVENTION

The present invention relates to a dental implant device and a method for using the same and in particular, to such a device and method in which the implant device projects the implant anchor's location, orientation and axis while facilitating the treatment of the peri-implant tissues.

BACKGROUND OF THE INVENTION

Dental implants are well known in the art and typically include a dental implant anchor securely inserted into the patient's jawbone, an abutment member attached to the dental anchor, and a prosthodontic restoration coupled thereon.

The method of implantation generally occurs over various stages where that generally initiates with the implant anchor's introduction into the jawbone and ends with loading the implant anchor with an abutment and restoration. There are a number of intermediates steps and procedures that are undertaken between the implant anchor's introduction and loading that can be spread over a three to nine month period.

The intermediate steps generally involve allowing the host tissue, gingiva and peri-implant tissues to heal and to be modeled in preparation for receiving the abutment and restoration. These intermediates steps are lengthy and require about eight individual medical procedures and/or iterations with a professional caregiver, where following each procedure and/or iteration requires a healing period.

Each intermediate steps requires different implant devices to facilitate the tissue healing and modeling process, for example cover screws, healing abutments, impression copings.

SUMMARY OF THE INVENTION

State of the art dental implant devices utilized during the intermediate steps of the implant procedure require multiple invasive and costly procedures.

Following the implantation of a dental implant anchor, the anchor is not easily discoverable following the healing period. This is due to that fact that during the healing process, the morphology of the gingival tissue covering the anchor is restored, making it difficult to locate and/or discover the underlying anchor. The exact location of the anchor is not known, nor readily visible to the practitioner. The approximate implant anchor site is estimated and thereafter located by way of surgical exploratory probing, often utilizing inaccurate surgical incisions.

During the anchor uncovering process much of the host tissue is needlessly lost. Such tissue loss can lead to various medical drawbacks for example, vertical bone loss, prolonged re-healing period, formation of closed and inaccessible voids, pockets, cysts, formation of fibrotic tissue, improper sealing possibly leading to contamination, overlapping of the anchor's margins with proliferated neo-tissue leading to inadequate abutment coupling and loosening.

Once the implant anchor is discovered the host tissue must be prepared for implant loading with various devices such as a healing abutment, to allow the peri-implant tissue to be modeled in preparation for implant anchor loading.

The dental implant device, system and method of use according to embodiments of the present invention provide for a non-invasive and a-traumatic method that remotely treats the peri-implant tissue to promote faster healing, while significantly reducing the number of procedures and caregiver iterations required between anchor implantation and loading. The dental implant device of the present invention further facilitates the implantation process by providing for readily identifying the location, orientation and axis of the implanted dental implant anchor in a non-invasive manner, for example by visual inspection. The dental implant device according to embodiments of the present invention further provides for minimizing peri-implant host tissue loss during the process of discovering and uncovering of the implant anchor, which takes place prior to implant loading.

Optionally and preferably the device according embodiments of the present invention provides for projecting the anchor's axis relative to surrounding structures for example including but not limited to anatomical structures, the opposing jaw, the same jaw, adjacent teeth or prosthodontic elements, morphological elements, or any combination thereof.

Optionally and preferably embodiments of the device according to the present invention provides for a minimally invasive and a-traumatic method for discovering and uncovering the implant anchor.

There is an unmet need for, and it would be highly useful to have, a dental implant device, system and method that provides for seamlessly discovering the implant's anchor. Moreover it would be highly advantageous to have an implantable device capable of identifying the anchor's position, orientation and axis while allowing for identifying a projection of the anchor, relative to surrounding prosthodontic elements and/or anatomic structures such as the teeth on the same and/or opposite jaw.

Furthermore optional embodiments according to the present invention may provide a platform on which an abutment assembly, or the like prosthodontics elements may be built.

Optionally prosthodontic elements may be coupled and/or otherwise associated with and/or functionally associated with the dental implant device of the present invention may for example include but is not limited to a transfer and/or attachment (ball attachment), abutment, the like or any combination thereof.

The dental implant device according to optional embodiments of the present invention may further provide for partial and progressive loading of the implanted anchor. Optionally the implant device according to optional embodiments of the present invention, most preferably while coupled with at least one or more optional prosthodontic elements, provides for progressive and/or gradual loading of the anchor, such that the anchor may be adjusted in dynamic relation to the progression and/or rate of bone remodeling and the healing process of the hard tissues.

Optional embodiments of the device of the present invention provides for facilitating treatment of the host tissue surrounding the implant therein providing for the maintenance, treatment and therapy of the host tissues. Preferably such treatment is accomplished in a non-invasive and a-traumatic manner without directly infiltrating the peri-implant and host tissue.

Optionally the device may comprise a treatment port and/or lumen to facilitate applying medical treatment to the surrounding host tissues. Therein optionally the device provides for at least one or more treatments of the host tissue with a flowing fluid for example including but not limited to applying and introducing medicaments, flowing fluids, gasses, antiseptics, irrigating fluids, antibiotics, probiotics, anesthetics, analgesics, dissolvable medicaments, evaporating medication the like or any combination thereof.

An optional embodiment of the present invention provides a dental implant device for associating with an implanted dental implant anchor immediately following implantation, the device provided for facilitating identifying the location, orientation and axis of the implanted dental anchor the device having a distal portion, a medial portion and an proximal portion that are defined between a distal end and a proximal end; the distal portion provided for securely associating the device with the dental implant anchor along the implant borehole; that is defined between the distal end and medial portion; the medial portion provided for covering the proximal end of the dental implant anchor; the proximal portion defined from the medial portion to the proximal end, provided for projecting the location, orientation and axis of implant anchor, characterized in that the proximal portion is a shaft extending proximally from the medial portion corresponding to the plane of the implant anchor's proximal end to assume the orientation and axis of anchor and to readily reveal the location of anchor by way of visual inspection.

Preferably the medial portion and the distal portion are screw form.

Optionally the proximal portion has a smaller diameter than medial portion.

Optionally at least a portion of the distal portion is configured and shaped according to the implant anchor's borehole to provide for coupling therewith.

Optionally the distal portion may be coupled with a mediating member to facilitate coupling with the implant anchor.

Optionally the device may be coupled with the implant anchor via a fixation screw.

Optionally the distal portion may be configured and shaped according to the implant anchor's anti-rotational connection platform aperture.

Optionally the medial portion may be shaped to complement the configuration of the anchor's proximal end so as to allow closure of the implant anchor's borehole Optionally the medial portion is configured to have an upper surface overlying the peri-implant tissue configured to act as a protective cover of the peri-implant tissues from tissue cutting.

Optionally the medial portion may comprise a lower surface configured to correspond to the distal end of the implant anchor.

Optionally the medial portion may comprise a peri-implant tissue collar portion configured to allow the peri-implant tissue to heal and to assume its final shape.

Optionally the collar portion may be configured and shaped according to the apical portion of the trans-gingival collar of a dental implant abutment.

Optionally and preferably the device features a continuous central channel disposed between the distal end to the proximal end. Optionally and preferably the channel features at least one or more openings along its length. Optionally and preferably the channel may be utilized for non-invasively and remotely introducing a flowing fluid for treating the peri-implant tissue.

Optionally external surface of proximal portion is configured to facilitate coupling with prosthodontic elements.

for example including but not limited to an abutment assembly, abutment, transfer, copying device, tools, dental hand piece, the like or any combination thereof.

Optionally the diameter of the proximal portion may be configured to be from about 1 mm to about 5 mm, 1 mm, 1.25 mm, 1.5 mm, 1.75 mm, 2.0 mm, 2.25 mm, 2.5 mm, 2.75 mm, 3.0 mm, 3.25 mm, 3.5 mm, 3.75 mm, 4.0 mm, 4.25 mm, 4.5 mm, 4.75 mm, 5 mm, including any from 1 mm to about 3 mm, 5 mm.

Optionally the external surface of proximal portion may be configured and shaped according to the implant anchor's anti-rotational connection platform.

Optionally the external surface of proximal portion may feature graduations or markings hat are indicative of height above the bone level.

Optionally the external surface of proximal portion comprises a reference marker along the length of proximal portion characterized in that the reference marker is correlated to the shape of the implant anchor's connection platform. Preferably the reference marker is indicative of and infers the implant anchor's orientation and the shape of the connection platform therein facilitating the implant impression coping and transfer process.

Optionally the shape of proximal portion, and particularly the external surface of the proximal portion is configured to reflect the shape of the implant anchor's connection platform.

An optional embodiment of the present invention provides a dental implant device for associating with an implanted dental implant anchor immediately following implantation, the device provided for facilitating identifying the location, orientation and axis of the implanted dental anchor following a healing period, the device having a distal portion, a medial portion and an interchangeable proximal portion; a) the distal portion provided for securely associating the device with the dental implant anchor along the implant borehole; the distal portion having a threaded channel disposed central within the distal portion body; the threaded channel provided for receiving and securely coupling with the proximal portion, the channel having threading selected from cylindrical threading or conical threading; b) the medial portion provided for covering the proximal end of the dental implant anchor; wherein the medial portion comprises a tooling aperture that is continuous with the distal portion threaded channel the tooling aperture provided in the form of anti-rotational tooling recess for manipulating the device; and c) the interchangeable proximal portion provided for projecting the location, orientation and axis of implant anchor; is a shaft having a diameter from about 1 mm to about 5 mm, that extends proximally from the plane of the implant anchor's proximal end to assume the orientation and axis of anchor; the proximal portion having a distal end including threading configured to complement and couple with the threaded channel threading.

An optional embodiment of the present invention provides for a dental implant system and/or kit including an optional implant device a mediating member, and a device cover and/or plug.

Optionally the system and/or kit may further comprise a tubular tissue punch provided for uncovering the gingival tissue overlying the dental implant anchor and dedicated driving tools for manipulating the implant device according to the present invention.

Optionally the system and/or kit may further comprise a gingival tissue depth measuring probe configured to measure the peri-implant tissue depth by inserting the probe into the proximal portion channel, the probe characterized in that it is shaped and configured according the luminal surface of channel; the probe having graduations or markings indicative of the probe height.

Optionally the measuring probe may have a length of up to about 15 mm.

An optional embodiment of the present invention provides a method for marking the position, axis and orientation of a dental implant anchor at the time of anchor placement so as to allow for: a-traumatic, minimally invasive uncovering of a dental implant anchor and to facilitating an impression coping of the dental implant anchor while reducing the number of procedures required to load the implant with a dental implant abutment, the method comprising: a) coupling a dental implant device according to the present invention with a dental implant anchor at the time of anchor placement; b) suturing the gingival tissue at the implantation site wherein the proximal portion extends above the gingival tissue level wherein the proximal portion provides for identifying the location and orientation of anchor by visual inspection; c) adjusting the length of the proximal portion relative to the gingival tissue by way of cutting or extending the proximal portion; d) apply a remote a-traumatic non-invasive tissue treatment of the peri-implant tissue through a proximal portion channel (420, 422) of the device; e) undertaking either a digital or analog impression coping of the implantation site wherein at least one of: a marker disposed on along the length of proximal portion, the external surface of proximal portion, inner luminal surface of channel, proximal end aperture, serve as a reference correlating and corresponding to the orientation and geometry of the anti-rotational connection platform aperture of implant anchor; f) a-traumatically anesthetizing the peri-implant tissue by introducing analgesics through proximal portion channel through at least one exit pore; g) uncovering the implant anchor and minimizing the peri-implant tissue loss over the implant anchor's occlusal portion by guiding a tissue punch device along the device's proximal portion; and h) disassociate device from anchor and proceed to load the implant with an abutment and restoration.

Optionally the method may further comprise associating a measuring probe with the device of the present invention within the lumen of a proximal portion channel prior to undertaking a digital impression by way of an oral digital scan and inferring from the scan the gingival tissue height.

An optional embodiment of the present invention provides a method for introducing a flowing fluid to the peri-implant tissues and host tissue surrounding an implant anchor using the implant device according to the present invention, the device is coupled to an implanted dental implant anchor for anesthetizing or irrigating the peri-implant tissue with the flowing fluid, the method comprising introducing the flowing fluid into the lumen and allowing the fluid to flow from the distal end through the exit pores disposed adjacent to the peri-implant tissues. The flowing fluid may for example include but is not limited to at least one or more of: medicaments, flowing fluids, gasses, antiseptics, irrigating fluids, antibiotics, probiotics, anesthetics, analgesics, dissolvable medicaments, evaporating medication, the like or any combination thereof.

An optional embodiment of the present invention provides a method for determining the peri-implant tissue depth by introducing a measuring probe into the lumen of implant device according to the present invention and obtaining a reading determining the lumen length utilized to infer the tissue depth.

An optional embodiment of the present invention provides a method for reducing the number of intermediate procedures required between a dental anchor placement to the abutment and restoration loading during a dental implant restoration procedure, the method comprising: a) Associating the implant device having a medial portion including a peri-implant collar portion, that is coupled with a dental implant anchor during implant anchor placement; b) Monitoring the healing of the gingival tissue while providing a-traumatic and minimally invasive treatment to the peri-implant tissue as needed via proximal portion channel, the treatment selected from, tissue irrigation, introduction of a medicament to the peri-implant tissue, shaping and protecting the peri-implant tissue with medial portion having a peri-implant collar; c) Facilitating digital or analog impression coping of the implantation site wherein the proximal portion of the implant device facilitates the identification of the orientation and geometry of the connection platform aperture of the implant anchor with at least one feature selected from: a marker disposed on along the proximal portion, the external surface of proximal portion, inner luminal surface of channel, proximal end aperture, the feature serves as a reference correlating and corresponding to the orientation and geometry of the anti-rotational connection platform aperture of implant anchor; d) a-traumatically anesthetizing the peri-implant tissue by introducing anesthetics from the proximal portion channel through at least one exit pore; e) uncovering the implant anchor and minimizing the peri-implant tissue loss over the implant anchor's occlusal portion by guiding a tissue punch device along the proximal portion of the implant device of the present invention; and f) disassociating the implant device from the anchor and proceeding to load the implant with an abutment and restoration.

Within the context of this application the term visual inspection refers to inspection by a user using only the unaided naked eye, that is without the use of any technological and/or computerized scanning means.

Within the context of this application the term prosthodontics elements is to refer to any elements utilized for dental implant restoration for example including but not limited to abutments, sleeves, interface members, transfers, restorations, impression copying, abutment extension, guide members, bistouries, scalpels over denture abutment, over denture attachment (for example, ball attachment), healing cap, any combination thereof or the like.

Unless otherwise defined, all technical and scientific terms used herein have the same meaning as commonly understood by one of ordinary skill in the art to which this invention belongs. The materials, methods, and examples provided herein are illustrative only and not intended to be limiting.

Implementation of the method and system of the present invention involves performing or completing certain selected tasks or steps manually, automatically, or a combination thereof.

There are many inventions described and illustrated herein. The present inventions are neither limited to any single aspect nor embodiment thereof, nor to any combinations and/or permutations of such aspects and/or embodiments. Moreover, each of the aspects of the present inventions, and/or embodiments thereof, may be employed alone or in combination with one or more of the other aspects of the present inventions and/or embodiments thereof. For the sake of brevity, many of those permutations and combinations will not be discussed separately herein.

As used herein, the indefinite articles "a" and "an" mean "at least one" or "one or more" unless the context clearly dictates otherwise.

Herein the term "proximal" generally refers to the side or end of a device that is intended to be closer to the performing practitioner, further from the location of the intervention. The term "distal" generally refers to the side or end of a device that is intended to be closer to or at the location of the intervention, and therefore further away from the performing practitioner.

Importantly, this Summary may not be reflective of or correlate to the inventions protected by the claims in this or continuation/divisional applications hereof. Even where this Summary is reflective of or correlates to the inventions protected by the claims hereof, this Summary may not be exhaustive of the scope of the present inventions.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in order to provide what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 2A-Q are schematic illustrative diagrams of optional implant device according to optional embodiments of the present invention; FIG. 2A-D show a perspective view of optional configurations of implant device; FIG. 2E-N show optional implant device featuring a fluid delivery channel; FIG. 2E shows an optional system featuring a measuring probe and a fluid delivery channel; FIG. 2I-K show an optional implant device featuring a peri-implant tissue protective segment; FIG. 2L-N show optional implant devices featuring a continuous open channel; FIG. 2O-Q show a top view of optional implant devices featuring optional reference markings;

FIG. 2R-S are schematic illustrative diagrams of an optional mediating members according to optional embodiments of the present invention;

FIG. 3A-B are schematic illustrative diagrams of optional implant device according to optional embodiments of the present invention;

FIG. 5A-B are schematic illustrative diagrams of optional dental implant tissue exposing device according to an optional embodiment of the present invention;

FIG. 6A-F are illustrative depictions of an exemplary method according to the present invention;

FIG. 8A-C are schematic illustrations of an extension member according to and optional embodiment of the present invention.

DESCRIPTION OF THE PREFERRED EMBODIMENTS

Figures 1A, 1B, 1C:
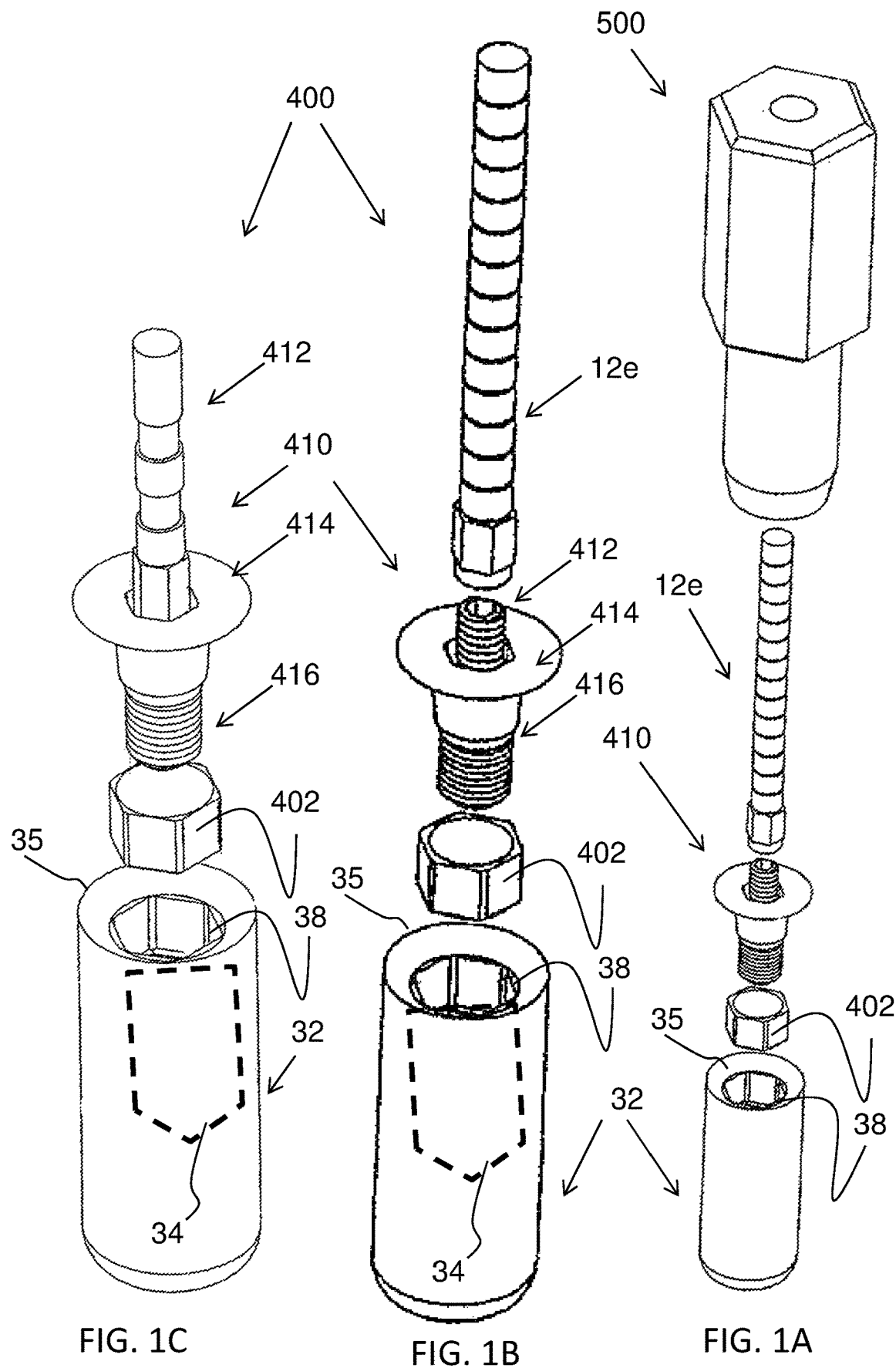
FIG. 1A-C are schematic illustrative diagrams of exemplary dental implant device and system according to optional embodiments of the present invention.

The present invention relates to a dental implant device and a method for using the same and in particular, to such a device and method in which the implant device provides a projection of the implant anchor's connection platform, location, orientation and axis while facilitating a-traumatic, non-invasive treatment of the peri-implant tissues from a remote location above the host peri-implant tissue.

The dental implant device, system and method of use according to embodiments of the present invention provide for a non-invasive and a-traumatic method that remotely treats the peri-implant tissue to promote faster healing, while significantly reducing the number of procedures and caregiver iterations required between anchor implantation and loading. The dental implant device of the present invention further facilitates the implantation process by providing for readily of identifying the location, orientation and axis of the implanted dental implant anchor in a non-invasive manner, for example by visual inspection. The dental implant device according to embodiments of the present invention further provides for minimizing peri-implant host tissue loss during the process of discovering and uncovering of the implant anchor.

The device of the present invention is preferably coupled with an implant anchor at the time of implant anchor placement and thereafter provides for reducing the number of intermediate procedures required between implant anchor placement and anchor loading, while facilitating non-invasive and a-traumatic care of the peri-implant tissues.

The device comprises a distal portion preferably for coupling with the implant anchor, a medial portion preferably for covering the distal end of the implant anchor, and a proximal portion preferably for projecting the implant anchor location, orientation and axis. Optionally the proximal portion provides for a non-invasive and a-traumatic care of the peri-implant tissues.

The present invention is of a dental implant device, system and a method of use during a dental implantation. Most preferably the dental implant device provides for allowing a practitioner to seamlessly discover the implant's anchor site, its orientation, and the anchor's axis by utilizing a projection thereof. Most preferably the device is discoverable by way of visual inspection without requiring unnecessary exploratory surgery to find the implant anchor.

Optional embodiments of the implant device of the present invention provides for facilitating treatment of the peri-implant tissue by way of remotely introducing a therapeutic agent and/or medicament to the host tissue surrounding the implant therein providing for the maintenance, treatment and therapy of the host tissues.

Optionally the implant device may comprise a treatment port channel for delivering a therapeutic agent to facilitate applying medical treatment to the surrounding host tissues, therein optionally providing for at least one or more treatments of the host tissue during the healing period following implantation. Therapeutic agents and/or substances that may be delivered and/or introduced through the port may for example include but is not limited to a therapeutic agent, flowing fluids, gasses, antiseptics, irrigating fluids, antibiotics, probiotics, anesthetics, analgesics the like or any combination thereof.

Preferably the device according to optional embodiments of the present invention provides for reducing the healing time and reduces the number of procedures required for a full dental restorative process, in particular during the intermediate stages between implant placement and implant loading.

The principles and operation of the present invention may be better understood with reference to the drawings and the accompanying description. The following figure reference labels are used throughout the description to refer to similarly functioning components are used throughout the specification hereinbelow.

| | |
|---|---|
| 12e | extension member; |
| 12t | extension member coupling threading; |
| 32 | anchor; |
| 34 | implant anchor internal borehole; |
| 35 | anchor proximal end or coronal end; |
| 38 | anchor aperture connection platform; |
| 400 | system; |
| 402 | mediating member; |
| 404 | mediating member; |
| 404a | external anti-rotational surface; |
| 404b | internal surface; |
| 406 | proximal portion measuring probe; |
| 408 | proximal portion cover/plug; |
| 410 | dental implant device; |
| 410d | distal end; |
| 410p | proximal end/occlusal end; |
| 412 | proximal portion/occlusal portion; |
| 412a | adjustment portion; |
| 412b | proximal base; |
| 412n | correlated external reference marking; |
| 412m | reference marker |
| 412r | anti-rotational aperture; |
| 412s | occlusal surface; |
| 412t | proximal threading; coupling |
| 414 | medial portion; |
| 414a | medial aperture; |
| 414b | abutment platform; |
| 414c | implant cover portion |
| 414p | peri-implant tissue collar; |
| 414n | narrow medial portion; |
| 414r | rimmed medial portion; |
| 414w | wide medial portion; |
| 416 | distal portion (anchor) portion; |
| 416a, b, d | distal couplers; |
| 416c | coupling portion; |
| 416s | sealing portion; |
| 416r | coupling recess |
| 416t | distal threading; |
| 416u | universal distal portion; |
| 420 | lumen/medicament channel port; |
| 420m | correlated inner luminal reference marker; |
| 420d | lumen distal end; |
| 420e | lumen exit pores; |
| 420p | lumen proximal end; |
| 422 | full channel; |
| 500 | anchor exposer; |
| 512 | distal portion; |
| 512s | exposing surface; |
| 514 | proximal end handle; |
| 516 | exposer central lumen; |

-continued

| | |
|---|---|
| 516d | distal end; |
| 516p | proximal end; |
| 518 | anchor projection guide; |
| 518b | guide base; |
| 518g | guide shaft; |

Now referring to FIG. 1A-C, FIG. 2E-F that show optional forms of a dental implant device 410 according to the present invention that functions as an integral member of system 400. Optionally system 400 may be provided in the form of a kit. Further optional systems are depicted in FIG. 2E-F showing system 400 comprising device 410 with a measuring probe 406, as shown in FIG. 2E, and a plug 408 as shown in FIG. 2F.

System 400 and kits thereof comprises device 410 and at least one additional member selected from mediating member 402 (FIG. 1A-C), mediating member 404 (FIG. 2R-S), guide 518 (FIG. 8C), measuring probe 406 (FIG. 2E), plug 408 (FIG. 2F), extension member 12 *e* (FIGS. 8A-B), and anchor exposing device 500 (FIG. 5A-B).

FIG. 1C shows system 400 comprising a device 410 and mediating member 402. Preferably mediating member 402 provides for interfacing and forming a seal with the internal lumen of dental implant anchor 32.

FIG. 1B shows system 400 similar to that of FIG. 1C however further comprising an extension member 12*e*, that will be described in greater detail in FIG. 8A-B. Extension member 12*e* facilitates utilizing device 410 in associating and building an abutment assembly thereon, for example the dental implant abutment assembly described in co-owned PCT Application No. PCT/IB2012/053829, incorporated herein by reference as if fully set forth.

FIG. 1A shows system 400 similar to that depicted in FIG. 1B however further comprising a dedicated tissue exposing device 500, described in greater detail in FIG. 5A-B. Most preferably anchor exposing device 500 is provided to perform precise incision and remove minimal amount of tissue necessary to uncover both the anchor's 32 location, orientation. Preferably exposing device 500 is characterized in that it may be guided toward the location anchor 32 by at least one of the proximal portion 412 of device 410 and/or an extension 12*e* associated therewith and/or a guide 518.

Most preferably device 410 and system 400 are provided to interface with a dental implant anchor 32 that has already been prepared and implanted in the jawbone as is known in the art. Optionally and preferably device 410 may be further provide for mediating and/or interfacing between both anchor 32 and an implant abutment (not shown).

The following description describing device 410 collectively and interchangeably refers to aspects of the dental device 410 as shown in FIG. 1-4.

Most preferably device 410 is generally a unitary screw form device having a proximal end 410*p* and a distal end 410*d* comprising three segments and/or portions, a proximal portion 412, a medial portion 414 and a distal portion 416. Most preferably the medial portion 414 and distal portion 416 take the screw-form, where medial portion takes the form of a screw-head and distal portion takes the form of a screw body, while proximal portion 412 is a rod like body that extends proximally from the medial portion 414. Optionally proximal portion 412 has a generally smaller diameter than the medial portion 414.

Optionally and preferably each portion of device 410 may be individually configured.

Optionally device 410 may be provided as a two piece device comprising a proximal portion 412 that may be securely fastened to a screw form body including the distal portion 416 and medial portion 414, characterized in that the distal portion and medial portion form a single body having a central a recess adapted for receiving and securely coupling with and optional proximal portion 412.

Most preferably device 410 comprises proximal portion 412 defining an occlusal extension, associated with an implant anchor 32 via distal portion 416 and medial portion 414. Such an occlusal extension 412 facilitates readily locating the implant anchor 32 while identifying the implant anchor's (32) orientation and axis of implantation within the bone by visual inspection following the healing period. Device 410 therefore affords to reduce the number of physician visits required, intermediate steps during implantation, following the initial anchor 32 placement from about eight visits to about two visits. Furthermore device 410 obviates the need for healing caps, healing abutments, coping transfer, and serves to streamline and reduce the overall dental implantation procedure.

Most preferably distal portion 416 provides for associating and/or coupling device 410 with an implanted anchor 32 along the anchor's internal lumen 34 that is usually utilized to couple an abutment and/or a fixation screw. Coupling may optionally be achieved by optional means for example including but not limited to threading, Morse angle, snap fit, friction fit, connectors, fixation screws or the like coupling means that is configured according to the anchor 32 utilized.

Distal portion 416 may comprise a coupling portion 416c and a sealing portion 416s, both provided to facilitate associating device 410 with anchor 32. Preferably coupling portion 416c and sealing portion 416s are configured according to the anchor's 32 borehole 34.

Optionally distal portion 416 may be provided in the form of a universal distal portion 416u that is devoid of sealing portion 416s and coupling portion 416t. Preferably universal distal portion 416u, FIG. 2N allows for associating device 410 with any anchor 32 utilizing a fixation screw (not shown) and a mediating member 404 (FIG. 2R-S) discussed in greater detail below.

Distal portion 416 may comprise coupling means in optional forms that are disposed along coupling portions 416c. Optionally coupling portion 416c may be provided in the form of threading 416t for example as shown in FIGS. 1A-C, 2A-D, 2F-K, 3A-B, 4A-4C and FIG. 4F.

Figure 4C:
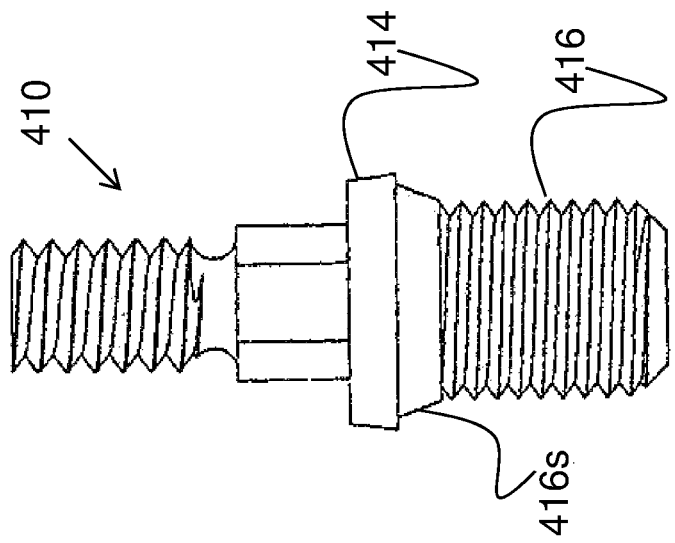
FIG. 4A-F are schematic illustrative diagrams of optional implant device of according to optional embodiments of the present invention.
Figure 4B:
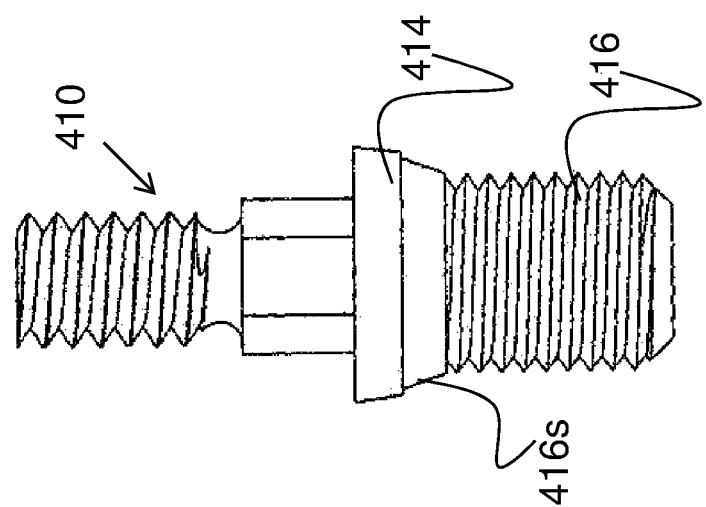
Figure 4A:
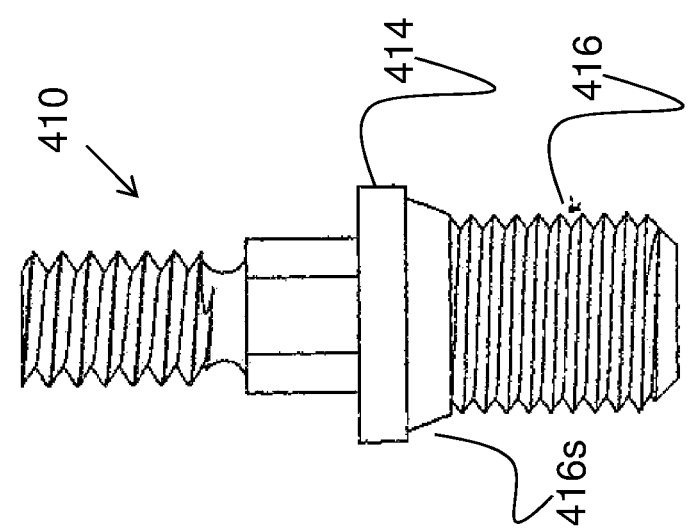
Figure 4F:
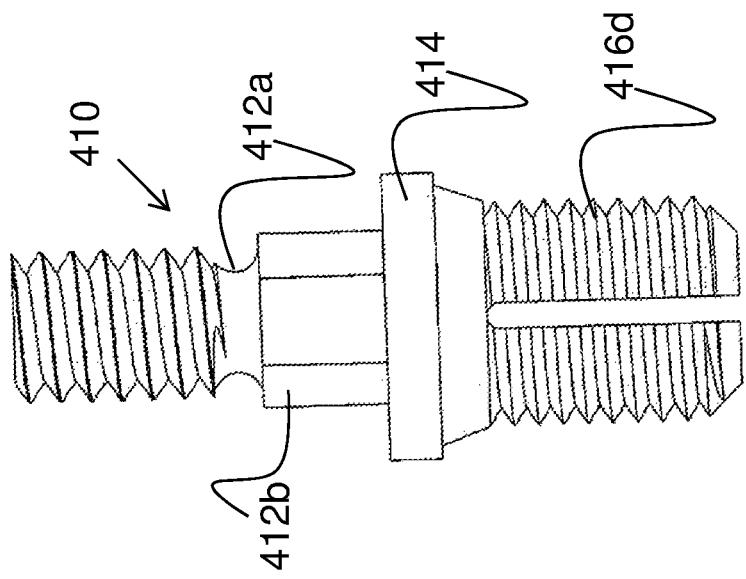
Figure 4E:
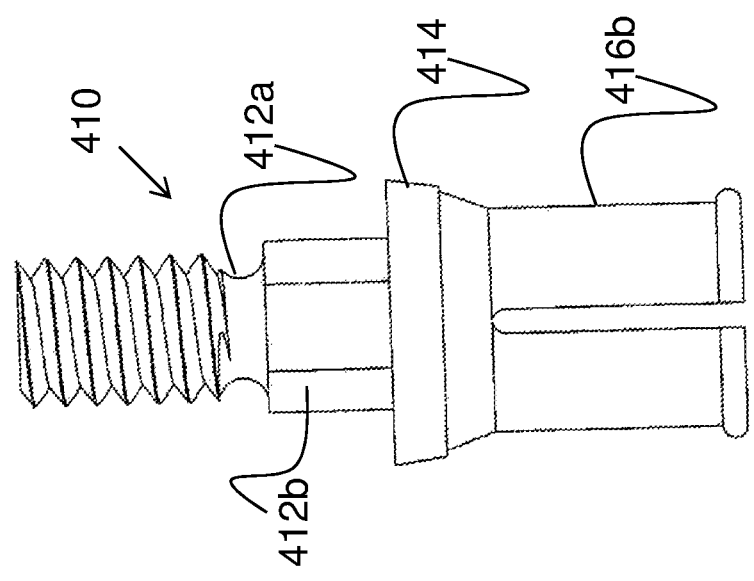
Figure 4D:
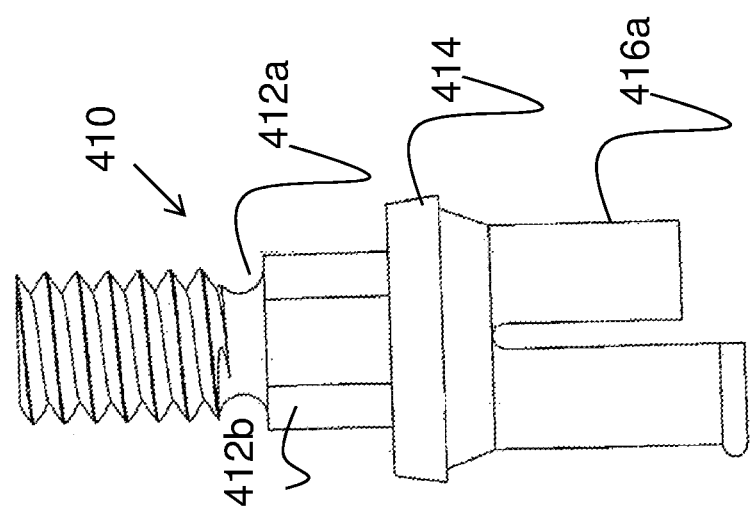

Optionally coupling portion 416c may be fit with snap fit distal coupling members 416a, b, d, for example as shown in FIG. 4D-F. Optionally distal coupling members 416a,b,d may be fit with threading for example as shown in FIG. 4F depicted distal coupling member 416d having both a snap fit configuration and threading. Optionally snap fit coupling member 416a,b,d may be adapted with an optional mediating member 402, 404 to assume other form coupling forms.

Figures 2L, 2M:
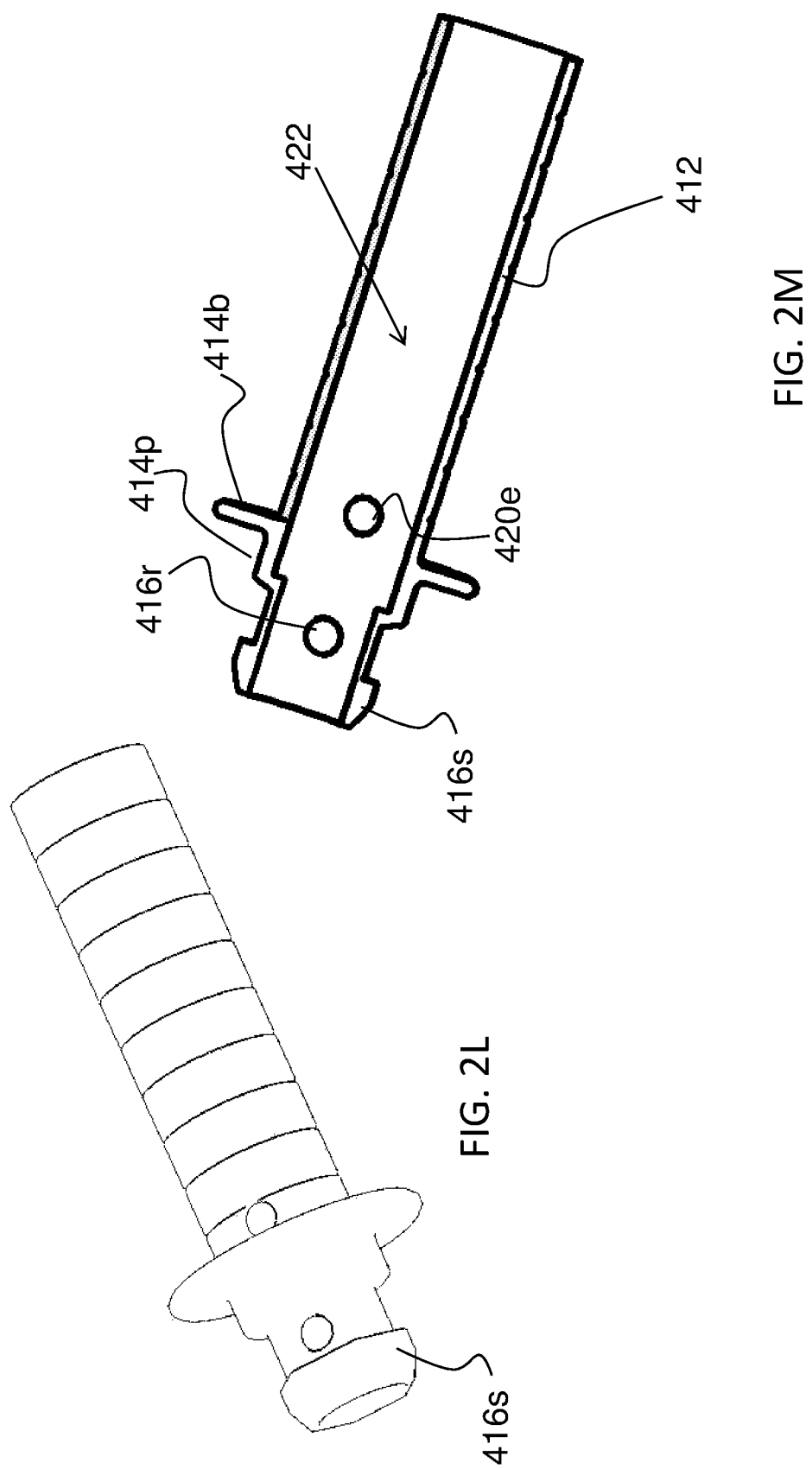

Optionally distal portion 416 may be devoid of threading, for example as shown in FIG. 2E and FIG. 2L-M. Distal portion 416 that are devoid of threading may be securely fastened to implant anchor 32 along borehole 34 threading with a fixation screw to securely couple device 410 to implant anchor 32. Optionally a fixation screw, not shown, may be introduced at the distal portion 416 through an open channel 422 spanning the length of device 410, for example as shown in FIG. 2M.

Optionally the sealing portion 416s of distal portion 416 may be configured according to anchor 32 and in particular the connection platform aperture 38 of anchor 32 and/or borehole 34 of anchor 32. For example as shown in FIG. 2L-N, the distal portion of sealing portion 416s is configured according to the geometry of the implant anchor's 32 connection platform 38. Such that sealing portion 416s matches the shape of connection platform 38. In such configuration distal portion 416 may be devoid of a coupling segment and may therefore be coupled with anchor 32 via a fixation screw (not shown).

Optionally and preferably sealing portion 416s may be configured according to at least one or more parameter for example selected from size, angle, shape, slope, surface, diameter, length or the like, or any combination thereof.

Optionally sealing portion 416s may be provided with optional surface configuration for example including but not limited to circular, oval, conical, polygonal of n sides where n is equal to at least 3 (n>2), lobular, tri-lobe, internal hex, external hex, internal octagonal, Morse, the like, any combination thereof, or the like connection platform as is known in the art.

Optionally sealing portion 416s may be configured to assume the anti-rotational connection platform 38 of anchor 32, for example as shown in FIG. 2L-FIG. 2M.

Optionally, the length of sealing portion 416s may be short, for example as depicted in FIG. 4A-F, or may be minimal to altogether removed as shown in FIG. 2D, for example, or may be of average and/or standard length for example as shown in FIG. 2A-C and FIG. 3A-B.

Optionally and preferably distal portion 416 and in particular sealing portion 416s may be further fit with and/or mediated to fit within borehole 34 of implant anchor 32 with an external sealing member for example in the form of mediating members 402, 404, for example as shown in FIG. 1A-C and FIG. 2R-S.

Optionally mediating member 402, 404 may be formed from biocompatible materials, titanium, silicone, sealing material, the like or any combination thereof. Most preferably mediating member 402, as shown in FIG. 1-C, provides for mediating between sealing portion 416s and the connection platform 38 and/or inner borehole 34 surface of anchor 32. Optionally and preferably the outer surface of mediating member 402 is provided to fit with and/or assume the inner borehole surface 34 or connection platform 38 of anchor 32.

Optionally distal portion 416 and in particular sealing portion 416s may feature at least one or more recess 416r along its external surface, for example as shown in FIG. 2G-2M. Preferably recess 416r is provided to facilitate sealing when utilizing a flexible mediating member 402, for example provided from flexible and/or shape deformable materials such as silicone. Preferably recess 416r is adapted to house portion of mediating member 402 when a flexible mediating member 402, for example made of silicone, is pressed between the external surface of sealing portion 416s and the internal borehole wall 34 of anchor 32. Accordingly, recess 416r provides for firmly associating and retaining device 400 within the borehole of anchor 32.

Varying views of an optional mediating member 404 are shown in FIG. 2R-S. Mediating member 404 is optionally provided from non-flexible biocompatible materials for example medical grade titanium, steel, alloys, polymers or the like biocompatible materials as is known in the art. Preferably mediating member 404 is provided to convert the distal portion 416 to correspond to and fit with the anti-rotational connection platform aperture 38 of an implant anchor 32. Optionally and preferably mediating member 404 may be utilized to convert a non-specific and/or universal distal portion 416 of device 410, for example in the form of a universal distal portion 416u, as shown in FIG. 2N.

Universal distal portion 416*u* is provided so as to allow device 410 to be non-selectively and/or universally fit into a plurality of dental implant borehole's 34. Mediating member 404 preferably has an external anti-rotational surface 404*a* that is specific to match the anti-rotational connection platform 38 of an implant anchor 32. Most preferably mediating member 404 is provided with an internal surface 404*b* configured to complement and/or to facilitate coupling to universal distal portion 416*u*. Accordingly, a universal portion 416*u* may be coupled with mediating member 404 along its internal surface 404*b* so as to allow a device 410 having universal distal portion 416*u* to specifically and securely with implant anchor 32 along it anti-rotational aperture 38.

Most preferably medial portion 414 is fluid with distal portion 416 and provides for covering the distal end 35 of anchor 32 as well as the connection platform aperture 38 of anchor 32. Optionally and preferably at least one surface of medial portion 414 is configured to assume the shape of distal end 35 having a generally planar circular configuration capable of covering distal end 35. Optionally medial portion 414 may be configured to be substantially cylindrical having varying diameters along the length of medial portion, for example as shown in FIG. 2I-K.

Optionally medial portion 414 may be configured to have a substantially cylindrical configuration, further provide for modeling and protection the peri-implant tissue to create a peri-implant collar adjacent to implant anchor 32.

Most preferably medial portion 414 provides for capping and/or sealing the distal opening 35 of anchor 32, and may therefore be configured according to the shape, size, geometry of the coronal portion 35 of anchor 32, particularly about its borehole aperture 38. Therein optionally medial portion 414 provides for covering the borehole of anchor 32, for example acting as a lid.

Optionally medial portion 414 may be provided in optional configurations and shape for example including but not limited to wide, narrow, thin, thick, or just in the form of a flange surface, the like, or any combination thereof. Optional formations and/or configurations of medial portion 414 are shown in FIG. 1-4. Specifically, FIGS. 1-2B and 3A show a wide medial portion 414*w*, configuration that assumes a flange discoid shape. FIG. 3B shows narrow medial portion 414*n*, while FIG. 2D shows rimmed medial portion 414*r*, having minimal profile.

Optionally and preferably medial portion 414 may be provided with optional profiles configured to fit with and correspond to anchor 32. For example, optional profiles of medial portion 414 are depicted in FIG. 4A-C, showing that the angle, slope and direction of medial portion 414 may be configured and vary, most preferably based on the configuration of anchor 32, particularly along borehole 34. FIG. 4A shows a cylindrical configuration of medial portion 414; FIG. 4B-C show trapezoidal configurations of medial portion 414 with opposite orientation.

Most preferably the occlusal surface of medial portion 414 may comprise an aperture 414*a*, as shown in FIG. 3A-B, configured with an anti-rotation geometry. Optionally and preferably the aperture 414*a* is provided to facilitate manipulating cover-screw 410 with corresponding tools, for example to couple cover-screw 410 to anchor 32.

Optionally and preferably aperture 414*a* may further provide an interface and/or recess for receiving a portion of an extension member 12*e*, or the like abutment portion.

Optionally medial portion 414 may be configured to model and/or mold the peri-implant tissue during the healing period and to protect the peri-implant tissue when uncovering the implant anchor 32. Most preferably the protective medial portion comprises an upper surface 414*b* for sheltering the underlying peri-implant tissue, a lower surface 414*c* for covering distal end 35 of anchor 32, and a peri-implant tissue collar portion 414*p* disposed therebetween provided a surface for modeling the peri-implant tissue during healing.

Preferably upper surface 414*b* overlies the peri-implant tissue configured to act as a protective cover of said peri-implant tissues from tissue cutting. Optionally upper surface 414*b* may be configured to have a diameter selected from about 2.5 mm up to about 10 mm, about 3 mm to about 7 mm, about 2 mm, about 5 mm, about 6 mm, up to about 10 mm, or the like.

Optionally the diameter of upper surface 414*b* may be configured according to at least one or more of implant anchor 32, abutment, tissue cutting device, tissue punch (500), the like or any combination thereof. Optionally the diameter of upper surface 414*b* may be configured to be larger than the diameter of tissue punch 500 (FIG. 5A-B).

Preferably lower surface 414*c* is configured to correspond to and/or match distal end 35 of implant anchor 32 wherein upper surface 414*b* is configured extending above the distal end 35 of implant anchor's 32, therein forming collar portion 414*p*.

Preferably peri-implant tissue collar portion 414*p* is configured to allow the peri-implant tissue to heal and to assume its final shape.

Optionally the external surface and shape of collar portion 414*p* may be configured and shaped according to the apical portion of the trans-gingival collar of a dental implant abutment. Optionally collar portion 414*p* may be configured to have a height of from about 0.3 mm up to about 4 mm, more preferably about 1 mm.

Optionally collar portion 414*p* may further comprises at least one or more exit port 420*e* for introducing a flowing fluid and/or medicament to the peri-implant tissue, as will be described in greater detail below.

Most preferably proximal portion 412 (also referred to as occlusal portion and/or occlusal extension) is disposed opposite the distal portion 416 and extending from and/or projecting from medial portion 414 toward proximal end 410*p*. Preferably proximal portion 412 is fluid and continuous with medial portion 414 and distal portion 416 forming a unitary device. Optionally proximal portion 412 may be coupled with a unitary distal portion 416 and medial portion 414 therein providing device 410 configured to have at least two parts.

Proximal portion 412 is an elongated shaft having a diameter from about 1 mm to about 5 mm, and a height that may be readily adjusted and/or cut to size during the anchor placement procedure such that it protrudes above the gum line after implant anchor implantation.

Proximal portion 412 most preferably provides for readily and visibly discovering the location, orientation and axis of anchor 32 following implantation and after the healing period, preferably by visual inspection. Therein device 410 having an elongated proximal portion 412 saves unnecessary prodding and/or exploratory surgery utilized today to find and identify the location of implant anchor 32 following the healing period.

Optionally, proximal portion 412 may further provide and facilitate the build-up of an abutment assembly onto anchor 32 via device 410. For example, proximal portion 412 may facilitate coupling anchor 32 with optional prosthodontics elements.

Optionally the proximal portion 412 may provide for associating with optional abutment assembly member for example including but not limited to extension member 12e (FIG. 8A-B) that may be utilized to form and build up an abutment assembly for example as described in co-owned PCT Application No. PCT/IB2012/053829.

Optionally proximal portion 412 may be utilized to interface and/or couple additional optional prosthodontic elements for example by way of threading. Optional prosthodontic element may for example include but is not limited to: impression coping, transfer, extension 12e, anchor guides (518, FIG. 8C), overdenture abutment, overdenture attachment, ball attachment, prosthetic elements, the like or any combination thereof.

Most preferably proximal portion 412 provides for interfacing an abutment assembly and dental restoration. Optionally and preferably proximal portion 412 may be configured according to at least one or more parameters for example including but not limited to shapes, sizes, clinical parameters, restoration parameters, abutment assembly parameters, the like or any combination thereof. For example as shown in FIG. 2-3 the proximal portion 412 may be configured to assume a plurality of optional configurations.

Most preferably proximal portion 412 provides an occlusal extension to anchor 32. Most preferably proximal portion 412 provides for identifying the location, orientation and axis of anchor 32.

Optionally the length of proximal portion 412 may be configurable. Optionally the length of proximal portion 412 may be long or short. Optionally the length of proximal portion 412 may be adjustable by way of milling and/or cutting its length with dental tools such as a dental hand piece. Optionally proximal portion 412 may be adjustable so as to assume a plurality of angles and/or configurations.

Optionally proximal portion 412 may be provided with a base 412b, for example as shown in FIG. 2A-D, 2F-G, 2J. Optionally and preferably base 412b extends occlusally beyond the occlusal surface of medial portion 414, as shown.

Optionally base 412b may be configured within medial portion 414, such that it does not extend beyond the surface of medial portion 414, for example as shown in FIG. 3B, within a recess and/or medial portion anti-rotational aperture 414a, as shown.

Optionally base 412b may be provided with an anti-rotation configuration, for example a hexagon as shown, so as to facilitate manipulation of device 410 with a tool. Optionally base 412b may be provided in any shape or anti-rotational configuration for example including but not limited to polygon of n sides where n is at least 3 or more, or the like as is known in the art.

Optionally proximal portion 412 may comprise threading 412t along its external surface, for example a shown in FIG. 1-A-B, 2A, 2D, 3A-B. Threading 412t is preferably provided to couple and/or otherwise associate with other prosthodontic restorative structures known in the art.

Optionally threaded proximal portion 412t may optionally comprise adjustment points 412a about its length, as shown in FIG. 2A, 2D. Optionally adjustment points 412a may provide for cutting and/or bending or the like manipulation of proximal portion 412.

Optionally threading 412t may provide for coupling with extension member 12e or a guiding member 518, shown in FIG. 8A-C, that may be utilized to extend the length of occlusal portion 412 or to act as a guiding member. Optionally and preferably extension member 12e, and guiding member 518 preferably comprise threading 12t corresponding threading 412t to facilitate coupling thereof.

Optionally threading 412t may be utilized to serve as a base onto which an abutment assembly, for example as disclosed in co-owned PCT Application No. PCT/IB2012/053829, may be built. Optionally an abutment assembly may be built onto a proximal portion 412 coupled with an extension member 12e along threading disposed along its length.

Optionally occlusal portion 412 may be provided with optional external surfaces 412s for example as depicted in FIG. 2A-N. Optionally external surface 412s may be provided with threading 412t (FIG. 2A,2D), anti-rotational shaped (FIG. 2E), smooth cylindrical (FIG. 2B,2F), graduation and/or markings 412m, 412n (FIG. 2N), segmentations (FIG. 2G), snap-ring coupling structure (FIG. 2C), coatings, bio-absorbable materials, respobable materials any combination thereof or the like.

Optionally proximal portion 412 may optionally comprise anti-rotational geometry aperture 412r disposed about its proximal end 410p, for example as shown in FIG. 3A-B, depicting two optional configurations. Optionally aperture 412r may provide for facilitating tool manipulation and/or facilitating abutment coupling.

Optionally proximal end 410p may comprise anti-rotational geometry along external surface 412s and/or along internal surfaces 412r, for example as shown in FIG. 2E. Optionally the external surface 412s or a portion thereof, for example in the form of markings 412n, may be configured to duplicate and/or replicate and/or reproduce the anti-rotational aperture 38 of anchor 32, above the gingiva, for example as shown with cover-screw 410 depicted in FIG. 2E. Most preferably in replicating aperture 38 of implant anchor 32 cover-screw 410 provides for projecting the direction, angle of implant anchor 32 and the shape of the connection platform aperture 38 to facilitating the transfer and impression process.

Optionally external surface 412s may be provided with external markings 412n configured to complement anti-rotational aperture 38 of anchor 32 so as to provide a reference correlated to the implant anchor's anti-rotational geometry, without having to remove gingival tissue to expose the implant anchor 32. FIG. 2O-P show a top view of external surface 412s comprising external reference markings 412n that are configured to correlate to the implant anchor's 32 anti-rotational connection platform aperture 38.

Optionally external surface 412s may feature external graduations and/or markings 412m, for example as shown in FIG. 2N. Optionally the markings or graduations 412m are indicative of height above the bone level where the implant 32 is placed. Optionally marking 412m may be shaped to facilitated identification and/or calculating the bone level height may for example be selected from triangular, trapezoidal or polygonal of n sides where n>2 or the like. Optionally markings or graduations 412m may be scored and/or etched and/or painted onto the external surface 412s.

Optionally the internal surface of proximal end 410p may form an aperture 412r at proximal end 410p that may be configured to duplicate and/or replicate and/or reproduce the anti-rotational aperture 38 of anchor 32, above the gingiva, for example as shown with cover-screw 410 depicted in FIG. 2E. Most preferably external surface 416s, as shown in FIG. 2E, provides for associating with anti-rotational aperture 38 of anchor 32, while external surface 412s having the shame shape mirrors that surface above the gingiva. Most preferably external surface 416s and 412s are configured to correspond with one another and to the anti-rotational aperture 38 of anchor 32 such that surfaces 416s and 412s effectively replicate the geometry, orientation and direction of aperture 38 and implant anchor 32.

Optionally proximal portion 412 may be configured to have an extendible compressed spring core, for example provided in a spring form for example a stent-like material such as nitinol that may extend the length of proximal portion over time. For example, proximal portion 412 may comprise spring like core that is compressed and configured to decompress and therefore expand proximally over time. Optionally the compressed spring core defining proximal portion 412 may be coated with bio-absorbable materials to define its external surface 412s, for example surface 412s may be formed from bio-absorbable sutures that undergo resorption over time gradually allowing the spring-core to decompressing and extend proximally, to reveal the location, orientation and axis of implant anchor 32.

Optionally distal portion 412 core may be realized as a self-inflating capsule that expands by osmotic principles.

Optionally device 410 may feature a central fluid lumen and/or channel 420,422 that may span from the proximal end 410p to the distal end 410d. Most preferably channel 420, 422 span the length of proximal end 412, preferably from proximal end 420p to base 412b, for example as shown in FIG. 2E-2N. Most preferably channels 420,422 comprise at least one or more exit pores 420e to allow for delivery of a flowing fluid introduced from the proximal 410p. Most preferably channel 420,422 facilitate non-invasively and a-traumatically, by remotely introducing a flowing fluid that may be utilized to treat the peri-implant host tissue.

FIGS. 2F and 2E shows a schematic illustration of an optional device 410 according to the present invention wherein proximal portion 412 comprises a channel 420 and a plurality of exit pores 420e that optionally and preferably provides for introducing a flowing fluid for example, a medicament and/or therapeutic agent, to the tissue surrounding anchor 32.

Optionally lumen 420 may span the length of cover-screw 410, for example spanning proximal end 410p to distal end opening 410d, and feature at least one or more exit pores 420e disposed along the length of device 410. Optionally exit pores 420e may be provided along at least one or more segment of device 410 for example proximal portion 412, medial portion 414, distal portion 416. Optionally medial portion 414 may comprise exit pores 420e along the peri-implant tissue collar 414p.

Optionally lumen 420 may span the length of proximal portion 412 of cover-screw 410, from proximal end 420p ending adjacent to medial portion 414, and features at least one or more exit pores 420e adjacent to medial portion 414 on the proximal portion 412.

Preferably lumen 420 facilitates applying medical treatment to the surrounding host tissues, therein optionally providing for at least one or more treatments of the host tissue for example including but not limited to applying and/or introducing medicaments, therapeutic agents, flowing fluids, gasses, antiseptics, irrigating fluids, antibiotics, probiotics, anesthetics, the like or any combination thereof.

Optionally and preferably lumen 420 may further allow for introducing retrograde flow of anesthetic material to infiltrate the host tissue adjacent to exit pores 420e, therein alleviates the need for multiple trans-gingival needle-prick near anchor 32.

Most preferably such retrograde flow allows therapeutic agent and/or materials, for example periochip, optionally deposited and/or stored and or placed within the lumen of anchor 32, to penetrate host tissues adjacent to exit pores 420e by way of retrograde flow where such therapeutic active agents flow from distal end 420d toward exit pores 420e through lumen 420.

Optionally channel 422 spanning the length of device 410, for example as shown in FIG. 2L-N, provides for introducing a fixation screw to couple device 410 to anchor 32. Optionally channel 420, 422 may be utilized to house a controlled release capsule and/or medicament adjacent to exit pores 420e to allow for controlled and time release of a therapeutic agents into the peri-implant tissue.

Optionally the internal surface of channel 420, 422 may feature a correlated inner luminal reference marker 420m, as shown in FIG. 2Q, configured to complement anti-rotational aperture 38 of anchor 32 so as to provide a reference correlated to the implant anchor's anti-rotational geometry, without having to remove gingival tissue to expose the implant anchor 32. FIG. 2Q shows a top view of channel 420, 422 comprising correlated reference markings 420m that are configured to correlate to the implant anchor's 32 anti-rotational connection platform aperture 38.

Optionally the internal surface of channel 420,422 may be configured to match the anti-rotational connection platform aperture 38, facilitating the transfer coping process.

Channel 420, 422 may be utilized to introduce a measuring probe 406, FIG. 2E, provided to determine the height of the gingival tissue. Preferably measuring probe 406 is shaped to match the shape of channel 422, 420. Optionally probe 406 is configured to a have a preset length of up to about 15 mm so as to act as a reference point for measuring the height of the gingival tissue. Optionally probe 406 may feature graduations or markings along its length indicative of the probe height.

Optionally channel 420, 422 may be plugged and/or covered at proximal end 420p with a plug and/or cover 408 for example as shown in FIG. 2F, depicting and optional system 400. Preferably plug 408 provides for closing the proximal open end 420p of channel 420,422.

Optionally lumen 420 and exit pores 420e may further provide a means and method for splinting and confining anchor 32 and cover-screw 410 to the maxilla, particularly over the maxillary sinus. Most preferably lumen 420 and exit pores 420e may be utilized to confine anchor 32 and cover-screw 410 disposed adjacent to maxillary sinus so as to prevent migration and loss of anchor 32 into the maxillary sinus cavity. Optionally exit pores 420e and lumen 420 may be utilized to introduce sutures, and/or fixation wires or the like, to suture and/or wire device 410 to the maxilla, most preferably to act as a stopper that prevents potential migration of anchor 32 into the maxillary sinus. Optionally a plurality of exit pores 420e in a single device 410 may be sutured and/or wired to the maxilla. Optionally a plurality of exit pores 420e spanning at least two or more, or more preferably a plurality of cover-screws 410, may be jointly sutured and/or wired to the maxilla, preferably to act as a stopper that prevents potential migration of anchor 32 into the maxillary sinus.

FIG. 5A-B shows views of an optional non-limiting configuration of anchor exposing and/or surfacing tool 500. FIG. 5A shows a perspective view while FIG. 5B shows the corresponding cross-sectional view.

Most preferably anchor exposing tool 500 is provided as a single piece device that may be manipulated manually. Optionally anchor exposer 500 may be configured to be associated with a manually manipulating handle and/or arm. Optionally exposer 500 may be coupled or otherwise associated with a motorized auxiliary device provided to facilitate its manipulation, for example including but not limited to a dental hand-piece, or the like.

Exposing tool 500 most preferably comprises a proximal portion having proximal portion 514 and a distal portion 512. Optionally and preferably distal portion 512 comprises a sharp exposing surface 512*s* provided for exposing and/or surfacing the anchor 32 from below the gingival surface. Exposing surface 512*s* is a sharp edge surface that facilitates cutting the gingival surface covering anchor 32.

Optionally exposer 500 may be configured to be as a single use disposable device. Optionally exposer 500 may be configured to be a multi-use device that may be readily sterilized for example by way of an autoclave.

Most preferably proximal portion 514 provides a manipulating handle that may be manipulated manually or utilized with additional tools for example a handle as previously described. Optionally and preferably proximal portion 514 is provided with a shape that may be readily handled by tools.

Most preferably anchor exposing device 500 comprises a continuously open lumen 516 spanning both proximal portion 514 and distal portion 512. Most preferably open lumen 516 may be shaped to facilitate receiving at least a portion of device 410 and/or anchor 32. More preferably distal end 516*d* of open lumen 516 may be configured and/or shaped and/or sized to receive a portion of anchor 32 and/or a distal portion 416 of device 410. More preferably proximal end 516*p* of open lumen 516 may be configured and/or shaped and/or sized to receive a proximal portion 412 of device 410.

Optionally exposer 500 may be associated with anchor axis projection guide 518, FIG. 8C, or proximal portion 412 of device 410 that provides for guiding exposer 500 toward anchor 32. Optionally exposer 500 is associated with guide 518 along guide shaft 518*g* or proximal portion 412 through lumen 516 allowing exposing surface 512*s* to be guided along shaft 518*g* or proximal portion 412 toward guide base 518*b* or medial portion 414 allowing surface 512*s* to come into contact with the gingival surface overlying anchor 32, therein most preferably minimizing the amount of host tissue lost in and around anchor 32 while exposing the anchor, therein alleviating the need for suturing, and significantly reducing the healing period.

Optionally exposing tool 500 may be provided in various sizes and shapes. Optionally the size and shape of exposer 500 may be provided relative to the size and/or diameter of the implant anchor 32 and/or cover-screw 410.

Figure 6B:
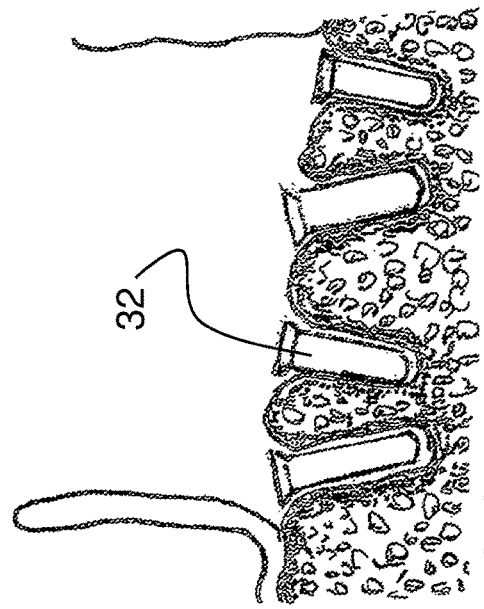
Figure 6D:
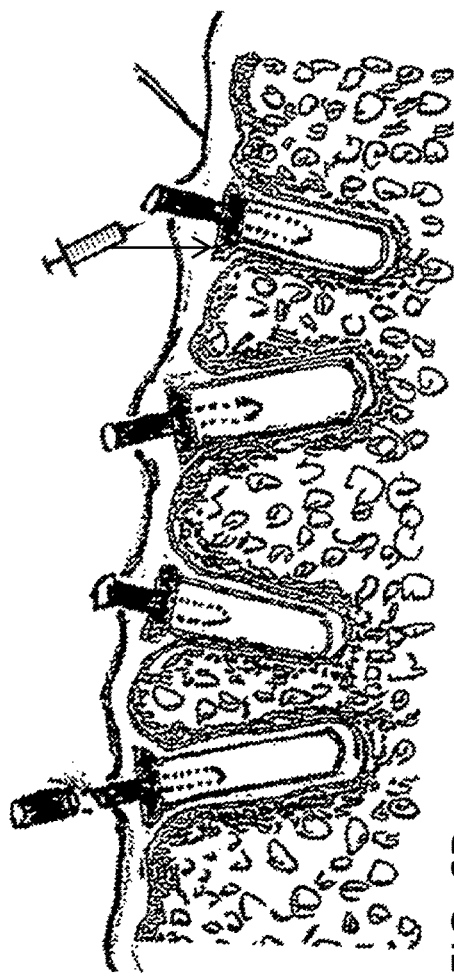
Figure 6A:
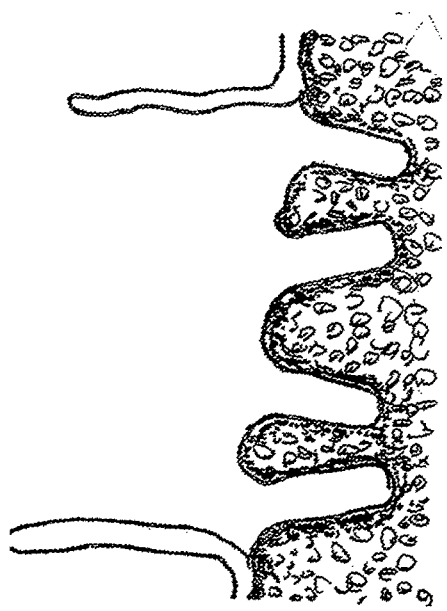
Figure 6C:
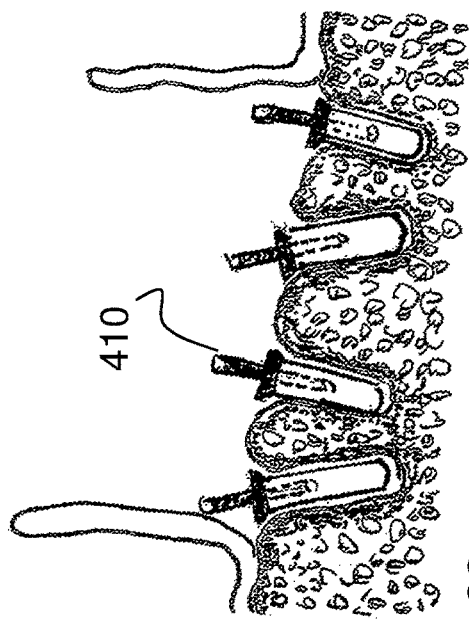
Figure 7:
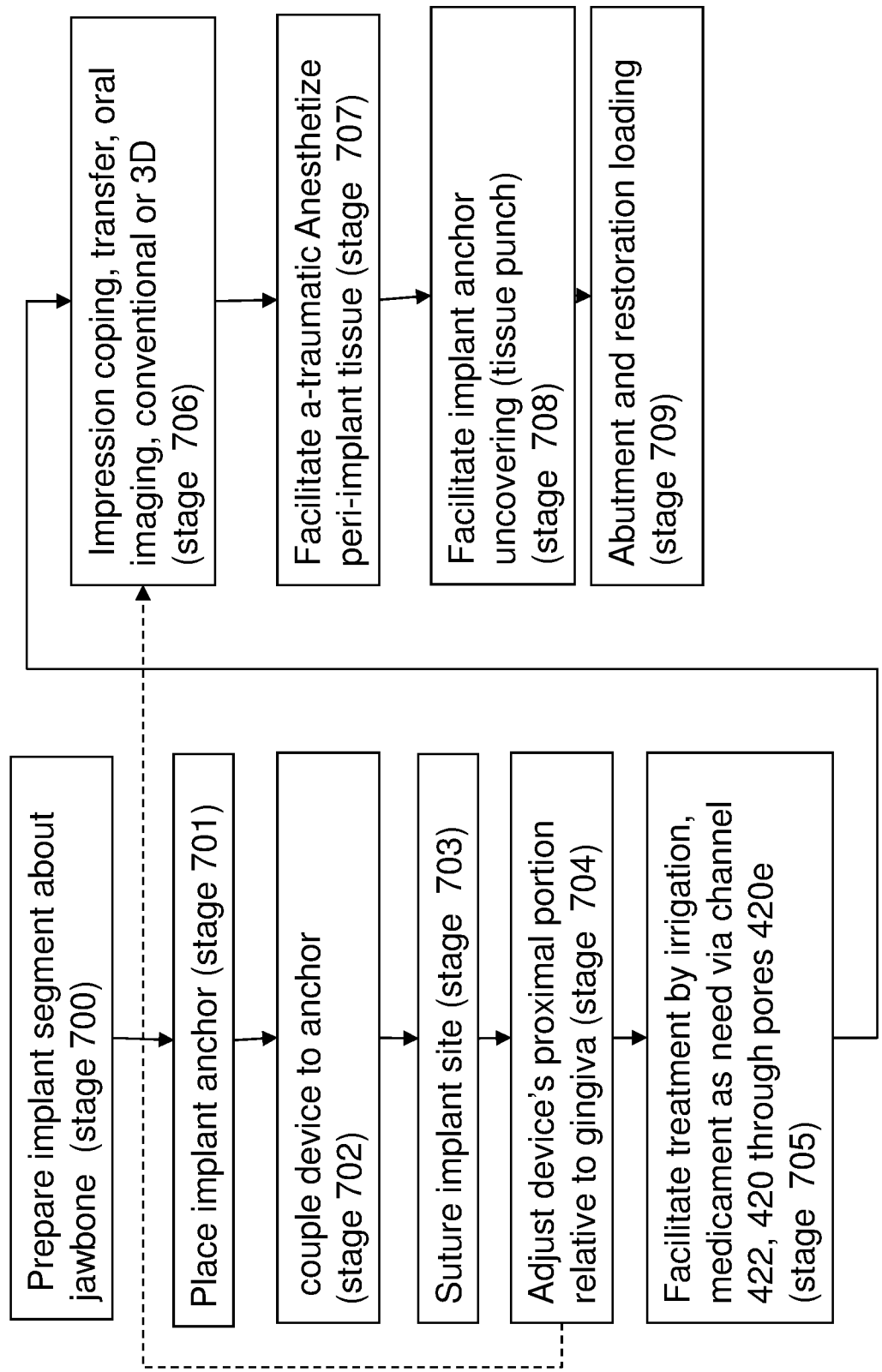
FIG. 7 is a flowchart of an exemplary method for utilizing the dental implant device and systems, as depicted in FIG. 6A-F according to an optional embodiment of the present invention.

FIG. 6A-F and FIG. 7 provide depiction of a preferred method according to the present invention for utilizing device 410 and system 400 provided to reduce the number of intermediate procedures and physician iterations required between implant anchor placement and implant loading. FIG. 7 provides a flowchart of the method while FIG. 6A-F provide corresponding schematic illustrations of the method.

First in stage 700 the implantation site is prepared, as is known in the art, for example as illustrated in FIG. 6A. FIG. 6A shows the initiation of the implantation process starts by exposing an implantation site by creating a gingival flap, for example a midline flap, as is known in the art. This is followed by creating of a recess (surgical alveoli) is formed for receiving a dental implant anchor 32 and implanting implant anchor 32 within the recess (surgical alveoli). Next in stage 701 and as shown in FIG. 6B, the anchor 32 is securely placed within the recess.

Next in stage 702 and as shown in FIG. 6C the anchor 32 is coupled with device 410 along the anchor's borehole 34 while covering distal end 35. Most preferably device 410 and in particular distal portion 416 is configured to fit securely with anchor 32 about borehole 34 and/or aperture 38, while medial portion 414, 414*c* is provided to cap the anchor's distal end 35, and allowing proximal portion 412 to project from the anchor's distal end 35.

Optionally distal portion threading 416*t* may be utilized to couple with the anchor's internal threading disposed along borehole 34. Optionally distal portion 416 may be coupled via a fixation screw introduced through channel 422. Optionally distal portion 416 may be coupled with anchor 32 utilizing a mediating member 402 to interface with recess 416*r*. Optionally distal portion 416*u* may be fit with mediating member 404 to correspond to connection platform aperture 38 while coupling to anchor 32 with a fixation screw.

Next in stage 703, as shown in FIG. 6D the implantation site and/or anchor site is closed to allow for healing.

Next in state 704, as shown in FIG. 6D, the proximal portion 412 of cover-screw 410 may be adjusted, sized and/or cut-down according to the needed level following closure of the implantation site.

Optionally proximal portion 412 may be left exposed above the gingival tissue and not cut down relative to the gingiva.

Optionally proximal portion 412 may be capped with cover 408. Optionally proximal portion 412 may be capped with filling material, temporary filling materials or the like.

Optionally proximal portion 412 is sized and exposed such that it does not interfere with the placement of a temporary restoration. Optionally an exposed proximal portion 412 may further constitute a lever for the surrounding elements to remove significant forces acting on anchor 32.

Optionally the gingival tissue may enclose over and/or cover the anchor and device 410 with the gingival flap such that the proximal end 412 of device 410 is covered and/or submerged beneath by the gingival tissue.

Optionally and most preferably the gingival tissue is sutured over to cover anchor 32 and cover-screw 410 such that at least a portion of the proximal end 412 of cover-screw 410 remains exposed during the healing phase, and therein protrudes through the gingival tissue. Optionally proximal end 412 exposed through the gingival surface may be coupled or otherwise associated with a dedicated cap 408.

Most preferably the proximal end 410*p* is adjusted relative to the gingiva so as to allow visualization of the anchor location, orientation and axis by visual inspection. Most preferably proximal end 410*p* of proximal portion 412 comprises correlated external reference marking 412*n*, 420*m* indicative of the connection platform aperture 38.

Optionally following sizing of proximal portion 412 in stage 704 an analog or digital impression of the oral cavity may be taken, as outlined in stage 706, so as to capture the position, orientation and axis of implant anchor 32 and connection platform aperture 38 from reference markings 412*n*, 420*m*, 412*r* therein facilitating the transfer and impression processes.

Next in stage 705 the implantation site may be allowed to heal as necessary as is known in the art. Preferably during the healing period the peri-implant tissue may be treated remotely via channels 420,422 to irrigate and/or introduce a medicament in and around the peri-implant tissue, that are delivered through exit pores 420*e*, for example as schematically shown in FIG. 6D. FIG. 6D depict remote and non-invasive introduction of a flowing fluid from a syringe to the peri-implant tissue as indicated with the positional arrow through channel 420, 422 via exit pores 420*e*.

Optionally when utilizing device 410 having medial portion comprising a peri-implant tissue collar portion 414*p*, as shown in FIG. 2I-K, the portion 414*p* provides for modeling the peri-implant tissues therein facilitating the healing process and obviating the need for a healing abutment.

Optionally healing period may not be required in an immediate loading configuration of anchor 32 and coverscrew 410 according to an optional embodiment of the present invention.

Next in stage 706, optionally and preferably following the healing periods, the impression and transfer process of the implantation site is facilitated with device 410. Device 410 may facilitated either digital or analog impression transfer of the implantation site. Impression coping and/or the transfer process is facilitated by device 410 in that exposure of the implant anchor 32 is not required to carry out the impression and transfer process, as is currently implemented in the art. Device 410 provides for maintaining implantation site without exposing anchor 32 by utilizing proximal portion 412 to remotely indicate the position, orientation and axis of anchor 32 and connection platform aperture 38. Most preferably reference markings 412n, 420m, 412r and/or external surface 412s are correlated to the shape and orientation of connection platform aperture 38 therein facilitating the transfer and impression processes by projection the configuration of aperture 38 on proximal portion 412 making it readily available.

Next in stage 707, following the healing process and impression of the implantation site, prior to the uncovering of the implant anchor 32 as depicted in stage 708, the peri-implant tissue may be remotely and a-traumatically anesthetized by delivering anesthesia via channel 420, 422, to the peri-implant tissue via exit pores 420e, for example as shown in FIG. 6E. FIG. 6E shows a syringe comprising anesthetics delivered to the peri-implant tissue, as shown by directional arrow, through proximal end 420p of channel 420.

Next in stage 708 the implant anchor 32 is uncovered by removing the gingival tissue above the anchor. Most preferably, device 410 provides for removing minimal tissue by providing tissue removal device 500 with a guide utilizing proximal portion 412, 518 to guide device 500 toward anchor 32, for example as shown in FIG. 6E. Exposer 500 provides for exposing the anchor directly in a minimally invasive manner that does not require poking and prodding as the implantation site is readily viewable due to the projection provided by proximal portion 412 of cover-screw 410. Most preferably minimal gingival tissue covering anchor 32 is excised with exposing surface 512s, FIG. 5A-B, to reveal anchor 32 and cover-screw 410, as they are received into proximal end lumen 516. Most preferably this further provides for saving gingival tissue while exposing the anchor both in its location and implantation axis.

Next in stage 709 the implant loading process is undertaken as is known in the art. Optionally and preferably device 410 is disassociated from anchor 32 allowing abutment loading as is known in the art.

Optionally device 410 comprising proximal end threading 412t may be retained and associated with anchor 32 to allow for an abutment assembly, an over denture attachment or additional prosthetic elements, may be built, coupled or otherwise associated directly onto cover-screw 410 about its proximal end 412 optionally utilizing extension member 12e, for example as shown in FIG. 6F. Optionally an abutment assembly may be built on proximal portion threading 412t and/or extension member 12e, for example as described in co-owned PCT Application No. PCT/IB2012/053829, incorporated herein by reference as if fully set forth.

Optionally exposer 500 may be utilized to facilitate abutment assembly buildup about proximal end 412. Optionally, distal end opening 516d and central lumen 516 may be utilized to facilitate introducing an optional extension member 12e to facilitate the initiating an abutment buildup about anchor 32, for example as shown in FIG. 6E-F.

While the invention has been described with respect to a limited number of embodiment, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

The foregoing is considered as illustrative only of the principles of the invention. Further, since numerous modifications and changes will readily occur to those skilled in the art, it is not described to limit the invention to the exact construction and operation shown and described and accordingly, all suitable modifications and equivalents may be resorted to, falling within the scope of the invention.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

Citation or identification of any reference in this application shall not be construed as an admission that such reference is available as prior art to the invention.

Section headings are used herein to ease understanding of the specification and should not be construed as necessarily limiting.

While the invention has been described with respect to a limited number of embodiments, it will be appreciated that many variations, modifications and other applications of the invention may be made.

What is claimed is:

1. A dental implant device configured for associating with an implanted dental implant anchor immediately following implantation, the device provided for facilitating identifying a location and axis of the implanted dental implant anchor following a healing period, the implanted dental implant anchor having a receiving borehole, the device is formed as a single piece device having a distal portion, a medial portion and a proximal portion that are defined between a distal end and a proximal end;

a. said distal portion is configured to securely associate said device with the implanted dental implant anchor with said receiving borehole; said distal portion defined between said distal end and said medial portion; wherein said distal portion is provided in screw form featuring a coupling portion and a sealing portion; and wherein said coupling portion is provided in the form of threading disposed adjacent to said distal end and configured for coupling with corresponding threading within said receiving borehole; and wherein said sealing portion is disposed adjacent to said medial portion; wherein said sealing portion features a mediating member made of flexible materials; and b. said medial portion having a cylindrical configuration and a diameter of about 2 mm; and
c. said proximal portion is defined from said medial portion to said proximal end and provided for projecting the location and axis of the implanted dental implant anchor such that the location and axis is revealed by way of visual inspection after the healing period, wherein said proximal portion has a smaller diameter than said medial portion; said proximal portion featuring:
  i. a base extending proximally from said medial portion and said base is provided with an anti-rotation configuration for manipulating said device; and
  ii. a vertically adjustable shaft is continuous with and extends proximally from said base toward said proximal end; said shaft is cylindrical having a diameter of up to about 1.5 mm along its length; and a smooth external surface; and wherein said vertically adjustable shaft may be cut at any location along the length of the shaft defined between said base to said proximal end.

2. The device of claim 1 wherein said shaft is a hollow shaft defining an open channel.

3. The device of claim 2 wherein said open channel comprises at least one channel exit pore.

4. The device of claim 3 wherein said at least one exit pore is disposed on said base.

5. The device of claim 3 wherein a location of said at least one exit pore is selected from:
  a. along the proximal portion;
  b. along the medial portion;
  c. along the proximal portion adjacent to the medial portion;
  d. at least one exit pore is disposed on the proximal portion and at least one exit pore disposed on the medial portion.

6. The device of claim 1 wherein said medial portion is configured to have an upper surface having a diameter that is larger than both the proximal portion and distal portion therein forming a flange overlying peri-implant tissue surrounding said dental implant anchor, therein said flange acting as a protective cover of said peri-implant tissue, wherein said diameter.

7. The device of claim 1 wherein said threading of said distal portion is configured to be conical threading.

8. The device of claim 1 wherein said mediating member is made of silicone.

9. The device of claim 1 wherein said sealing portion features at least one recess.

10. A dental implant device configured for associating with an implanted dental implant anchor immediately following implantation, the device provided for facilitating identifying a location and axis of the implanted dental implant anchor following a healing period, the implanted dental implant anchor having a receiving borehole, the device is a single piece device having a distal portion, a medial portion and a proximal portion that are defined between a distal end and a proximal end;
  a. said distal portion configured to securely associate said device with the implanted dental implant anchor with said receiving borehole; said distal portion defined between said distal end and said medial portion; wherein said distal portion is provided in screw form featuring a coupling portion and a sealing portion; and wherein said coupling portion is provided in the form of threading disposed adjacent to said distal end, and configured for coupling with corresponding threading within said receiving borehole; and wherein said sealing portion is disposed adjacent to said medial portion; and
  b. said medial portion having cylindrical configuration and a diameter of about 2 mm; and
  c. said proximal portion defined from said medial portion to said proximal end, provided for projecting the location and axis of the implanted dental implant anchor such that the location and axis is revealed by way of visual inspection after the healing period, wherein said proximal portion has a smaller diameter than said medial portion; said proximal portion featuring:
    i. a base extending proximally from said medial portion and said base is provided with an anti-rotation configuration for manipulating said device; and
    ii. a vertically adjustable shaft is a continuous elongated cylindrical hollow shaft having a smooth external surface, the shaft extends proximally from said base toward said proximal end, said hollow shaft having an external diameter of up to about 1.5 mm along its length and characterized in that said shaft defines an open channel featuring at least one channel exit pore provided for a-traumatic fluid delivery to peri-implant tissue via the proximal end; and wherein said vertically adjustable shaft may be cut at any location along the length of the shaft defined between said base to said proximal end.

11. The device of claim 10 wherein a location of said at least one exit pore is selected from:
  a. along the proximal portion;
  b. along the medial portion;
  c. along the proximal portion adjacent to the medial portion;
  d. at least one exit pore is disposed on the proximal portion and at least one exit pore disposed on the medial portion; and
  e. along said base.

* * * * *